(12) United States Patent
Nakatsuji et al.

(10) Patent No.: US 10,196,609 B2
(45) Date of Patent: Feb. 5, 2019

(54) COMPOSITION FOR PROMOTING CARDIAC DIFFERENTIATION OF PLURIPOTENT STEM CELL COMPRISING EGFR INHIBITOR

(71) Applicant: Kyoto University, Kyoto-shi (JP)

(72) Inventors: Norio Nakatsuji, Kyoto (JP); Itsunari Minami, Kyoto (JP)

(73) Assignee: KYOTO UNIVERSITY, Kyoto-Shi, Kyoto (JP)

(*) Notice: Subject to any disclaimer, the term of this patent is extended or adjusted under 35 U.S.C. 154(b) by 0 days.

(21) Appl. No.: 14/772,991

(22) PCT Filed: Feb. 5, 2014

(86) PCT No.: PCT/JP2014/052673
§ 371 (c)(1),
(2) Date: Sep. 4, 2015

(87) PCT Pub. No.: WO2014/136519
PCT Pub. Date: Sep. 12, 2014

(65) Prior Publication Data
US 2016/0002600 A1   Jan. 7, 2016

(30) Foreign Application Priority Data
Mar. 8, 2013   (JP) ................. 2013-046591

(51) Int. Cl.
C12N 5/077   (2010.01)

(52) U.S. Cl.
CPC ........ *C12N 5/0657* (2013.01); *C12N 2500/95* (2013.01); *C12N 2501/11* (2013.01); *C12N 2501/415* (2013.01); *C12N 2501/727* (2013.01); *C12N 2506/02* (2013.01); *C12N 2506/45* (2013.01)

(58) Field of Classification Search
CPC ............ C12N 2500/95; C12N 2501/11; C12N 2501/415; C12N 2501/727; C12N 2506/02; C12N 2506/45; C12N 5/0657
USPC ................................................. 435/375, 377
See application file for complete search history.

(56) References Cited

U.S. PATENT DOCUMENTS

| | | | |
|---|---|---|---|
| 4,970,318 A | 11/1990 | Schnur et al. | |
| 8,658,425 B2* | 2/2014 | Nakatsuji | C07D 277/82 435/243 |
| 2003/0134859 A1 | 7/2003 | Amemiya et al. | |
| 2006/0276393 A1 | 12/2006 | Milburn et al. | |
| 2007/0134215 A1 | 6/2007 | Fukuda et al. | |
| 2007/0148185 A1 | 6/2007 | Rathore et al. | |
| 2007/0149466 A1 | 6/2007 | Milburn et al. | |
| 2009/0068742 A1 | 3/2009 | Yamanaka | |
| 2009/0170914 A1 | 7/2009 | Bornancin et al. | |
| 2010/0183565 A1 | 7/2010 | Laflamme et al. | |
| 2012/0244619 A1 | 9/2012 | Nakatsuji et al. | |
| 2013/0183753 A1 | 7/2013 | Nakatsuji et al. | |
| 2013/0274215 A1 | 10/2013 | Thies et al. | |
| 2014/0127807 A1 | 5/2014 | Nakatsuji et al. | |
| 2014/0329311 A1* | 11/2014 | Laflamme | C12N 5/0657 435/325 |
| 2015/0017718 A1 | 1/2015 | Nakatsuji et al. | |
| 2015/0284683 A1* | 10/2015 | Shim | C12N 5/0657 435/377 |
| 2016/0002600 A1 | 1/2016 | Nakatsuji et al. | |

FOREIGN PATENT DOCUMENTS

| | | |
|---|---|---|
| EP | 2014766 A1 | 1/2009 |
| JP | S63-190880 A | 8/1988 |
| JP | H02-017181 A | 1/1990 |
| JP | 2000-508919 A | 7/2000 |
| JP | 2001-510450 A | 7/2001 |
| JP | 2004-535199 A | 11/2004 |
| JP | 2005-330443 A | 12/2005 |
| JP | 2006-218035 A | 8/2006 |
| JP | 2007-252220 A | 10/2007 |
| JP | 2009-500357 A | 1/2009 |
| JP | 2009-531365 A | 9/2009 |
| WO | 1997/41209 A1 | 11/1997 |
| WO | 98/17267 | 4/1998 |
| WO | 01/83427 A1 | 11/2001 |
| WO | 03/006950 A2 | 1/2003 |
| WO | 2005/037845 A1 | 4/2005 |
| WO | 2007/069666 A1 | 6/2007 |
| WO | 2007/070964 A1 | 6/2007 |
| WO | 2008/118820 A2 | 10/2008 |
| WO | 2009/006930 A1 | 1/2009 |
| WO | 2009/006997 A1 | 1/2009 |
| WO | 2009/007852 A2 | 1/2009 |
| WO | 2011/002950 A1 | 1/2011 |

(Continued)

OTHER PUBLICATIONS

Hu and Li Molecular Cancer 2010, 9:236.*
Paige et al. (PLoS One, Jun. 2010, vol. 5, Issue 6, pp. 1-8).*
Wang et al. (2009) Med. Biol. Eng. Comput. vol. 47, pp. 41-48.*
Shen, G., et al., "A 2,6-Disubstituted 4-Anilinoquinazoline Derivative Facilitates Cardiomyogenesis of Embryonic Stem Cells", ChemMedChem, 2012, 7, pp. 733-740.
Takayuki Morisaki, "Shinkinbunka niokeru bunshi kaibogakuteki seigyokiko no kaimei nikansuru kenkyu", Annual report of the research on cardiobascular diseases, Jan. 2005, p. 177.
Wang, Z., et al., "Neuregulin-1 enhances differentiation of cardiomyocytes from embryonic stem cells", Med. Biol. Eng. Comput., 2009, 47, pp. 41-48.

(Continued)

*Primary Examiner* — Janet L Epps-Smith
(74) *Attorney, Agent, or Firm* — K&L Gates LLP

(57) ABSTRACT

The present invention provides a composition for promoting cardiac differentiation of a pluripotent stem cell containing an EGFR inhibitor. The present invention also provides a kit for promoting cardiac differentiation containing an EGFR inhibitor and a method for inducing cardiac differentiation of a pluripotent stem cell comprising culturing the pluripotent stem cell in a medium containing an EGFR inhibitor.

14 Claims, 10 Drawing Sheets

(56) References Cited

FOREIGN PATENT DOCUMENTS

| WO | 2011/071118 A1 | 6/2011 |
|---|---|---|
| WO | 2011/127164 A2 | 10/2011 |
| WO | 2012/026491 A1 | 3/2012 |
| WO | 2013/111875 A1 | 8/2013 |
| WO | 2014/136519 A1 | 9/2014 |
| WO | WO-2015/037706 A1 | 3/2015 |

OTHER PUBLICATIONS

Translation of Internal Search Report issued in PCT/JP2014/052673, dated Apr. 28, 2014.
Translation of International Preliminary Report on Patentability issued in PCT/JP2014/052673, dated Dec. 2, 2014.
Laflamme, M.A. & Murry, C.E. Heart regeneration. Nature 473, 326-335 (2011).
Lluis Frederic, et al., "Periodic Activation of Wnt/?-Catenin Signaling Enhances Somatic Cell Reprogramming Mediated by Cell Fusion", Cell Stem Cell, 2008, Vol.3, p. 493-507.
Lutolf, M.P., Gilbert, P.M. & Blau, H.M. Designing materials to direct stem-cell fate. Nature 462, 433-441 (2009).
Menasche, P. Stem cell therapy for heart failure: are arrhythmias a real safety concern? Circulation 119, 2735-2740 (2009).
Mignone, J.L., Kreutziger, K.L., Paige, S.L. & Murry, C.E. Cardiogenesis from human embryonic stem cells. Circ J 74, 2517-2526 (2010).
Murakami, G. et al. Chemical library screening identifies a small molecule that downregulates SOD1 transcription for drugs to treat amyotrophic lateral sclerosis. J Biomol Screen 16, 405-414 (2011).
Naito, A.T. et al. Developmental stage-specific biphasic roles of Wnt/beta-catenin signaling in cardiomyogenesis and hematopoiesis. Proc Natl Acad Sci U S A 103, 19812-19817 (2006).
OA dated Apr. 29, 2014 issued in Chinese Patent Application 201180051572.7 along with its English translation.
Otsuji, T.G. et al. Progressive maturation in contracting cardiomyocytes derived from human embryonic stem cells: Qualitative effects on electrophysiological responses to drugs. Stem Cell Res 4, 201-213 (2010).
Paige, S.L. et al. Endogenous Wnt/beta-catenin signaling is required for cardiac differentiation in human embryonic stem cells. PLoS One 5, e11134 (2010).
Passier, R., van Laake, L.W. & Mummery, C.L. Stem-cell-based therapy and lessons from the heart. Nature 453, 322-329 (2008).
Qyang, Y. et al. The renewal and differentiation of Isl1+ cardiovascular progenitors are controlled by a Wnt/beta-catenin pathway. Cell Stem Cell 1, 165-179 (2007).
Rajala, K., Pekkanen-Mattila, M. & Aalto-Setala, K. Cardiac differentiation of pluripotent stem cells. Stem Cells Int 2011, 383709 (2011).
Ren, Y. et al. Small molecule Wnt inhibitors enhance the efficiency of BMP-4-directed cardiac differentiation of human pluripotent stem cells. J Mol Cell Cardiol 51, 280-287 (2011).
Sato, A., Kawazoe, Y., Kamisuki, S. & Uesugi, M. Synthesis of synthetic small molecule transcription factors (STF). Nucleic Acids Symp Ser (Oxf), 29-30 (2006).
Sato, S., Murata, A., Shirakawa, T. & Uesugi, M. Biochemical target isolation for novices: affinity-based strategies. Chem Biol 17, 616-623 (2010).
Segers, V.F. & Lee, R.T. Stem-cell therapy for cardiac disease. Nature 451, 937-942 (2008).
Smith, K. P. et al., Pluripotency: toward a gold standard for human ES and iPS cells, J Cell Physiol 220, 21-29 (2009).
Srivastava, D. & Ivey, K.N. Potential of stem-cell-based therapies for heart disease. Nature 441, 1097-1099 (2006).
Haraguchi, Y., "O-33-6 Hito iPS saibo no fuyubaiyohou oyobi shinkinsaibo heno bunkayudohou no kentou", Saiseiiryo, vol. 11, suppl Jun. 1, 2012, p. 211.
Suemori, H. & Nakatsuji, N. Generation and characterization of monkey embryonic stem cells. Methods Mol Biol 329, 81-89 (2006).

Suemori, H. et al. Establishment of embryonic stem cell lines from cynomolgus monkey blastocysts produced by IVF or ICSI. Dev Dyn 222, 273-279 (2001).
Suessbrich, H., Waldegger, S., Lang, F. & Busch, A.E. Blockade of HERG channels expressed in Xenopus oocytes by the histamine receptor antagonists terfenadine and astemizole. FEBS Lett 385, 77-80 (1996).
Wada Keiki et al., "Hito Tanosei Kansaibo Kabu (ES Oyobi iPS Saibo Kabu) o Mochiita Bunka Yudo Gijutsu Oyobi HTS eno Oyo Tenkai", Medicine and Drug Journal, 2010, vol.46, S-1, pp. 247-253.
Willems, E. et al. Small-molecule inhibitors of the Wnt pathway potently promote cardiomyocytes from human embryonic stem cell-derived mesoderm. Circ Res 109, 360-364 (2011).
Xu, Y., Shi, Y. & Ding, S. A chemical approach to stem-cell biology and regenerative medicine. Nature 453, 338-344 (2008).
Yamashita, J.K. ES and iPS cell research for cardiovascular regeneration. Exp Cell Res 316, 2555-2559 (2010).
Yoshida, Y. & Yamanaka, S. iPS cells: a source of cardiac regeneration. J Mol Cell Cardiol 50, 327-332 (2011).
Zhu, W. et al. IGFBP-4 is an inhibitor of canonical Wnt signalling required for cardiogenesis. Nature 454, 345-349 (2008).
Office Action dated Aug. 3,2015 issued in U.S. Appl. No. 14/374,453.
Biechele et al, Porcupine homolog is required for canonical Wnt signaling and gastrulation in mouse embryos, Developmental Biology 355 (2011) 275-285.
Okita et al, Induced pluripotent stem cells: opportunities and challenges, Phil. Trans. R. Soc. B (2011) 366, 2198-2207.
Yamashita, J., "Differentiation of cardiovascular cells from iPS cells", Igaku no Ayumi, Dec. 31, 2011, vol. 239, No. 14, pp. 1416-1421.
Fukuda, K., "Hito iPS saibo yurai saiseishinkin wo mochiita shinfuzen chiryoho no kakuritsu", May 15, 2012, 42(5), pp. 559-563.
Mummery et al., "Differentiation of Human Embryonic Stem Cells to Cardiomyocytes: Role of Coculture With Visceral Endoderm-Like Cells", Circulation, American Heart Association, 2003, 107, pp. 2733-2740.
Notarianni E. et al., "Derivation of pluripotent, embryonic cell lines from the pig and sheep", J. Reprod. Fert. Suppl. 43: 255-260 (1991)).
Notarianni E. et al., "Maintenance and differentiation in culture of pluripotential embryonic cell lines from pig blastocysts", Journals of Reproduction & Fertility 41: 51-56 (1990).
Yuasa, S., "ES saibo, iPS saibo karano shinkinbunka", Japanese Circulation Society, vol. 17, No. 2, Sep. 2009, pp. 223-229.
Sci Planner 2013, Chemical Abstracts Service, Columbus, OH,: RN-1118807-13-8 Downloaded Sep. 24, 2013.
Sci Planner 2013, Chemical Abstracts Service, Columbus, OH,: RN-349132-98-5 Downloaded Sep. 27, 2013.
Shamblott, et al., "Derivation of pluripotent stem cells from cultured human primordial germ cells" Proc. Natl. Acad. Sci. USA vol. 95, pp. 13726-13731, Nov. 1998.
Shi et al., "Induction of Pluripotent Stem Cells from Mouse Embryonic Fibroblasts by Oct4 and Klf4 with Small-Molecule Compounds", Cell Stem Cell 3(5): 568-574 (2008).
Talbot N. C. et al., "Culturing the epiblast cells of the pig blastocyst", Cell. Dev. Biol. 29A: 543-554 (1993).
Yu, J. et al. Induced pluripotent stem cell lines derived from human somatic cells. Science 318, 1917-1920 (2007).
Yuasa, S. et al. "Transient inhibition of BMP signaling by Noggin induces cardiomyocyte differentiation of mouse embryonic stem cells". Nat Biotechnol 23, 607-611 (2005).
Zhao et al., "Two Supporting Factors Greatly Improve the Efficiency of Human iPSC Generation", Cell Stem Cell 3: 475-479 (2008).
Zhou et al., "Generation of Induced Pluripotent Stem Cells Using Recombinant Proteins", Cell Stem Cell 4(5): 381-384 (2009).
Extended European Search Report dated Aug. 7, 2015 issued in the corresponding European Patent Application No. 13740826.6.
Minami, I., et al., "O-2-3 Shinkiteibunshikagoubutsu wo mochiita hitoES/iPSsaibo no rinsho gread shinkinbunkayudoho no kaihatsu", Saiseiiryo vol. 12 Suppl. 2013, p. 151.

(56) References Cited

OTHER PUBLICATIONS

Extended European Search Report dated Feb. 17, 2014 issued in the related European application No. 11819954.6.
Yang, L., et al., "Human cardiovascular progenitor cells develop from a KDR+ embryonic-stem-cell-derived population", Nature, vol. 453(7194), pp. 524-528 (2008).
Leschik J., et al., "Cardiac commitment of primate embryonic stem cells", Nature Protocol, vol. 3, No. 9, pp. 1381-1387 (2008).
Paul W. Burridge, et al., "A Universal System for Highly Efficient Cardiac Differentiation of Human Induced Pluripotent Stem Cells That Eliminates Interline Variability", PLos One, vol. 6, Issue 4, e18293 (2011).
Wang, H., et al., "Cardiac Induction of Embryonic Stem Cells by a Small Molecule Inhibitor of Wnt/b-Catenin Signaling", ACS Chemical Biology, 6(2), pp. 192-197 (2011).
Iwamoto, R., et al., "Heparin-binding EGF-like growth factor and ErbB signaling is essential for heart function", PNAS, vol. 100, No. 6, pp. 3221-3226 (2003).
Minami, I., et al., "A Small Molecule that Promotes Cardiac Differentiation of Human Pluripotent Stem Cells under Defined, Cytokine- and Xeno-free Conditions", Cell Reports, Nov. 29, 2012, d(5), pp. 1448-1460.
Graichen et al., "Enhanced cardiomyogenesis of human embryonic stem cells by a small molecular inhibitor of p38 MAPK", Differentiation (2008) 76:357-370.
Xu et al., "Chemically defined medium supporting cardiomyocyte differentiation of human embryonic stem cells", Differentiation (2008) 76:958-970.
Carlton et al., "Discovery of small molecule agonists for the bombesin receptor subtype 3 (BRS-3) based on an omeprazole lead", Bioorganic & Medicinal Chemistry Letters, 2008, vol. 18, No. 20, pp. 5451-5455.
Bellasio et al., "Substances with potential cardiovascular activity. 2-Acylaminobenzimidazoles with hypotensive activity", Farmaco, Edizione Scientifica, 1973, vol. 28, No. 2, pp. 164-182.
Harsanyi et al., "Reactions of acylcyanamides. I. New synthesis of 2-acylaminobenzoxazoles", Annali di Chimica (Rome, Italy), 1964, vol. 54, No. 11, pp. 1060-1065.
Database Registry [online]:Chemical Abstracts Service, Columbus, Ohio, USA. [retrieved on Feb. 19, 2013] Retrieved from STN, Registry Number(Entry Date): 1177562-46-7(Aug. 30, 2009), 1136531-24-2(Apr. 19, 2009) , 1136432-3.4-2(Apr. 19, 2009) , 1023259-74-6(May 28, 2008).
Toyama, "ES Saibo×iPS Saibo kara no Shinkin Saibo Bunka×Seisei×Ishoku", Japanese Journal of Transplantation, 2009, vol. 44, No. 3, pp. 219-225.
Yamauchi, K., et al., "Cardiomyocytes develop from anterior primitive streak cells induced by b-catenin activation and the blockage of BMP signaling in hESCs", Genes to Cells, 2010, 15, pp. 1216-1227.
Thomson et al., "Embryonic Stem Cell Lines Derived from Human Blastocysts", Science, 1998, 282, pp. 1145-1147.
Suemori et al., "Efficient establishment of human embryonic stem cell lines and long-term maintenance with stable karyotype by enzymatic bulk passage", Biochemical and Biophysical Research Communications, 2006, 345, pp. 926-932.
Thomson et al., "Isolation of a primate embryonic stem cell line", Proc. Natl. Acad. Sci. USA, 1995, vol. 92, pp. 7844-7848.
Thomson et al., "Pluripotent Cell Lines Derived from Common Marmoset (*Callithrix jacchus*) Blastocysts1", Biology of Reproduction, 1996, 55, pp. 254-259.
Doetshman et al., "Establishment of Hamster Blastocyst-Derived Embryonic Stem (ES) Cells", Developmental Biology, 1988, 127,224-227.
Evans et al., "Derivation and Preliminary Chabacterization of Pluripotent Cell Lines From Porcine and Bovine Blastocysts", Theriogenology, 1990, vol. 33, No. 1, pp. 125-128.
Piedrahita et al., "On the Isolation of Embryonic Stem Cells: Comparative Behavior of Murine, Porcine and Ovine Embryos", Theriogenology, 1990, vol. 34, No. 5, pp. 879-891.
Saito et al., "Bovine embryonic stem cell-like cell lines cultured over several passages", Roux's Arch Dev Biol, 1992, 201, pp. 134-141Bovine embryonic stem cell-like cell lines cultured over several passages.
Sukoyan et al., "Isolation and Cultivation of Blastocyst-Derived Stem Cell Lines From American Mink (Mustela vision)", Molecular Reproduction and Development, 1992, 33, pp. 418-431.
Kim et al., "Pluripotent stem cells induced from adult neural stem cells by reprogramming with two factors", Nature, 2008, vol. 454, pp. 646-650.
Kim et al., "Oct4-Induced Pluripotency in Adult Neural Stem Cells", Cell, 2009, 136, pp. 411-419.
Huangfu et al., "Induction of pluripotent stem cells from primary human fibroblasts with only Oct4 and Sox2", Nature Biotechnology, 2008, vol. 26, pp. 1269-1275.
Feng et al., "Reprogramming of fibroblasts into induced pluripotent stem cells with orphan nuclear receptor Esrrb", Nature Cell Biology, 2009, vol. 11, pp. 197-203.
Hanna et al., "Direct Reprogramming of Terminally Differentiated Mature B Lymphocytes to Pluripotency", Cell, 2008, 133, pp. 250-264.
Takahashi et al., "Induction of Pluripotent Stem Cells from Adult Human Fibroblasts by Defined Factors", Cell, 2007, 131, pp. 861-872.
Stuckwisch et al., "Some N-Substituted Dimethoxyphenylacetamides and Dimethoxyphenylethylamines", J. Med. Chem. (1965) 8(5): 734-735.
Search result of STN-Registry data base for "RN:308294-59-9", "RN:349132-90-7", "RN:805285-70-5", "RN:349438-98-8", "RN:953930-37-5", "RN:953995-50-1" and "RN:953993-61-8", Mar. 2014.
Asai, Y., Tada, M., Otsuji, T.G. & Nakatsuji, N. Combination of functional cardiomyocytes derived from human stem cells and a highly-efficient microelectrode array system: an ideal hybrid model assay for drug development. Curr Stem Cell Res Ther 5, 227-232 (2010).
Berge ten Derk, et al., "Embryonic stem cells require Wnt proteins to prevent differentiation to epiblast stem cells", Nature Cell Biol., 2011, vol. 13, No. 9, p. 1070-1075.
Burridge, P.W. et al. A universal system for highly efficient cardiac differentiation of human induced pluripotent stem cells that eliminates interline variability. PLoS One 6, e18293 (2011).
Chen, B. et al. Small molecule-mediated disruption of Wnt-dependent signaling in tissue regeneration and cancer. Nat Chem Biol 5, 100-107 (2009).
Chien, K.R., Domian, I.J. & Parker, K.K. Cardiogenesis and the complex biology of regenerative cardiovascular medicine. Science 322, 1494-1497 (2008).
Chien, K.R., Moretti, A. & Laugwitz, K.L. Development. ES cells to the rescue. Science 306, 239-240 (2004).
Even, M.S., Sandusky, C.B. & Barnard, N.D. Serum-free hybridoma culture: ethical, scientific and safety considerations. Trends Biotechnol 24, 105-108 (2006).
English Translation of IPRP dated Jul. 29, 2014 issued in corresponding International Application No. PCT/JP2013/051644.
English Translation of IPRP dated Mar. 19, 2013 issued in corresponding International Application No. PCT/JP2011/069054.
English Translation of ISR issued in corresponding International Application No. PCT/JP2013/051644 (dated 2013).
Gonzalez Rodolfo, et al., "Stepwise Chemically Induced Cardiomyocyte Specification of Human Embryonic Stem Cells", Angew. Chem. Int. Ed., 2011, vo1.50, p. 11181-11185.
Gotea, V. & Ovcharenko, I. DiRE: identifying distant regulatory elements of co-expressed genes. Nucleic Acids Res 36, W133-139 (2008).
Hansson, E.M., Lindsay, M.E. & Chien, K.R. Regeneration next: toward heart stem cell therapeutics. Cell Stem Cell 5, 364-377 (2009).
Hao, J. et al. Dorsomorphin, a selective small molecule inhibitor of BMP signaling, promotes cardiomyogenesis in embryonic stem cells. PLoS One 3, e2904 (2008).

(56) References Cited

OTHER PUBLICATIONS

Ichida, J.K. et al. A small-molecule inhibitor of tgf-Beta signaling replaces sox2 in reprogramming by inducing nanog. Cell Stem Cell 5, 491-503 (2009).
Irion, S., Nostra, M.C., Kattman, S.J. & Keller, G.M. Directed differentiation of pluripotent stem cells: from developmental biology to therapeutic applications. Cold Spring Harb Symp Quant Biol 73, 101-110 (2008).
Jacot, J.G., Martin, J.C. & Hunt, D.L. Mechanobiology of cardiomyocyte development. J Biomech 43, 93-98 (2010).
Kamisuki, S. et al. A small molecule that blocks fat synthesis by inhibiting the activation of SREBP. Chem Biol 16, 882-892 (2009).
Kattman, S.J. et al. Stage-specific optimization of activin/nodal and BMP signaling promotes cardiac differentiation of mouse and human pluripotent stem cell lines. Cell Stem Cell 8, 228-240 (2011).
PubChem CID 2694580—National Center for Biotechnology Information, PubChem Compound Database; CID=2694580, http://pubchem.ncbi.nlm.nih.gov/summary/summary.cgi?cid=2694580 (accessed Dec. 21, 2015), create date Jul. 16, 2005.
PubChem CID 2641096—National Center for Biotechnology Information, PubChem Compound Database; CID=2641096, http://pubchem.ncbi.nlm.nih.gov/summary/summary.cgi?cid=2641096 (accessed Dec. 21, 2015), create date Jul. 16, 2005.
PubChem CID 1358256—National Center for Biotechnology Information, PubChem Compound Database; CID=1358256, http://pubchem.ncbi.nlm.nih.gov/summary/summary.cgi?cid=1358256 (accessed Dec. 21, 2015), create date Jul. 11, 2005.
PubChem CID 1220560—National Center for Biotechnology Information, PubChem Compound Database; CID=1220560, http://pubchem.ncbi.nlm.nih.gov/summary/summary.cgi?cid=1220560 (accessed Dec. 21, 2015), create date Jul. 10, 2005.
PubChem CID 8582409—National Center for Biotechnology Information, PubChem Compound Database; CID=8582409, http://pubchem.ncbi.nlm.nih.gov/summary/summary.cgi?cid=8582409 (accessed Dec. 21, 2015), create date Jul. 30, 2006.
Ronca, R. et al., "Fibroblast growth factor receptor-1 phosphorylation requirement for cardiomyocyte differentiation in murine embryonic stem cells", J. Cell. Mol. Med. vol. 13, No. 8A, 2009 pp. 1489-1498.
Zhou, X. et al., "Differentiation of nonbeating embryonic stem cells into beating cardiomyocytes is dependent on downregulation of PKCβ and ζ in concert with upregulation of PKCε", Developmental Biology 255 (2003) 407-422.
Ventura, C. et al., "Protein Kinase C Signaling Transduces Endorphin-Primed Cardiogenesis in GTR1 Embryonic Stem Cells", Circulation Research, 2003, 92, pp. 617-622.
Hakuno, D. et al., "Focal Adhesion Kinase Signaling Regulates Cardiogenesis of Embryonic Stem Cells", Journal of Biological Chemistry, V. 280, No. 47, Nov. 25, 2005, pp. 39534-39544.
Morisaki, Takayuki, "Shinkinbunka ni okeru bunshikaibogakutekiseigyokiko no kaimeinikansuru kenkyu", Annual Report of the Research on Cardiovascular Diseases (Heisei 15 Nendo), National Cardiovascular Center, Jan. 2005, p. 177.
English Translation of International Preliminary Report on Patentability Chapter I, issued in the corresponding international application No. PCT/JP2015/065643 dated Dec. 6, 2016.
International Search Report issued in the corresponding international application No. PCT/JP2015/065643 dated Aug. 25, 2015.
Lian, X., et al., "Robust cardiomyocyte differentiation from human pluripotent stem cells via temporal modulation of canonical Wnt signaling", Proc. Natl. Acad. Sci. USA 109, E1848-E1857, 2012.
International Search Report and Written Opinion dated Dec. 9, 2014 issued in International Application No. PCT/JP2014/074233.
English translation of International Preliminary Report on Patentability dated Mar. 15, 2016 issued in International Application No. PCT/JP2014/074233.
U.S. Appl. No. 13/777,765, filed Feb. 26, 2013, Method for Promoting Differentiation of Pluripotent Stem Cells Into Cardiac Muscle Cells.
U.S. Appl. No. 14/154,765, filed Jan. 14, 2014, Method for Promoting Differentiation of Pluripotent Stem Cells Into Cardiac Muscle Cells.
U.S. Appl. No. 14/374,453, filed Jul. 24, 2014, Method for Inducing Cardiac Differentiation of Pluripotent Stem Cell.
U.S. Appl. No. 15/314,409, filed Nov. 28, 2016, Method for Inducing Cardiac Differentiation of Pluripotent Stem Cell With Low-Molecular Compounds.
Database Registry[Online]: Chemical Abstracts Service, Columbus, Ohio, USA. [retrieved on Oct. 7, 2011] Retrieved from STN, Registry Number(Entry Date): 1177562-46-7(Aug. 30, 2009), 1147532-35-1(May 19, 2009), 1147404-38-3(May 19, 2009) ,1147337-80-1 (May 19, 2009) , 1136531-24-2 (Apr. 19, 2009), 1136432-34-2(Apr. 19, 2009), 1090781-93-3(Dec. 28, 2008), 1061194-02-2(Oct. 14, 2008), 1061020-56-1 (Oct. 14, 2008), 103114438-3 (Jun. 27, 2008), 1031127-32-8(Jun. 27, 2008), 1023259-74-6(May 28, 2008), 1017145-50-4(Apr. 25, 2008), 94186424-0 (Jul. 10, 2007), 941861-12-7 (Jul. 10, 2007), 940726-30-7 (Jul. 2, 2007), 940660-05-9 (Jul. 2, 2007), 930893-80-4 (Apr. 19, 2007), 930520-52-8(Apr. 17, 2007), 930496-97-2(Apr. 17, 2007), 930025-45-9 (Apr. 13, 2007).

\* cited by examiner

COMPOSITION FOR PROMOTING CARDIAC DIFFERENTIATION OF PLURIPOTENT STEM CELL COMPRISING EGFR INHIBITOR

TECHNICAL FIELD

The present invention relates to a composition for promoting cardiac differentiation of a pluripotent stem cell containing an epidermal growth factor receptor (EGFR) inhibitor. The present invention also relates to a kit for promoting cardiac differentiation containing an EGFR inhibitor and a method for inducing cardiac differentiation of a pluripotent stem cell comprising culturing the pluripotent stem cell in a medium containing an EGFR inhibitor.

BACKGROUND ART

A technology to induce differentiation of pluripotent stem cells holds the key for realization of regenerative medicine and establishment of in vitro evaluation of drug efficacy and safety. In particular, the regenerative medicine and drug evaluation for heart diseases, which are the second cause of death in Japan, are important. Additionally, stable provision of homogenous cardiomyocytes is needed for cardiotoxicity study of various drugs since many drugs induce severe cardiac side effects including cardiac arrest and arrhythmia.

It has been reported that cardiac muscle differentiation of human ES/iPS cells is induced by co-culturing human ES cells and mouse feeder cells, END2 cells (Non Patent Literature 1, the reference is incorporated herein by reference). Unfortunately, the differentiation efficiency is low and the resulting human cardiomyocytes are not pure because of contamination of the mouse END2 cells.

It is also reported that cardiac muscle differentiation of human ES/iPS cells is induced by preparing embryoid from ES cells and adding several cytokines (fibroblast growth factor (FGF), bone morphogenetic protein 4 (BMP4), vascular endothelial cell growth factor, DKK1, Activin A) to the embryoid (Non Patent Literatures 2 and 3, the references are incorporated herein by references). It is also reported that cardiac muscle differentiation is induced with BMP4, FGF2, insulin and serum (Non Patent Literature 4, the reference is incorporated herein by reference). These methods, however, are not suitable for practical use due to need of huge amount of cytokines which increases cost. It is also reported that cardiac muscle differentiation of mouse ES cells is induced with XAV939, a tankyrase inhibitor (Non Patent Literature 5, the reference is incorporated herein by reference). Unfortunately, it is difficult to use the resulting cells for regenerative medicine since serum is used in the preparation of the cells and the differentiation efficiency is low as 10 to 60%.

The inventors of the present invention have reported low molecular weight compounds that promote cardiac differentiation of pluripotent stem cells (Patent Literatures 1 and 2, and Non Patent Literature 7, the references are incorporated herein by references).

Epidermal growth factor (EGF) receptor (EGFR) is a receptor tyrosine kinase, the ligand of which is EGF. EGFR is important for regulating proliferation, differentiation and maintenance of cells. EGF signaling has been reported to play an important role in development of heart (Non Patent Literature 6, the reference is incorporated herein by reference). EGFR is also involved in proliferation and metastasis of cancer cells. EGFR inhibitors such as gefitinib are used as an anti-cancer agent. However, use of EGFR inhibitors such as gefitinib and AG1478 has not been reported for inducing cardiac differentiation of human pluripotent stem cells.

CITATION LIST

Patent Literature

Patent Literature 1: WO2011/071118
Patent Literature 2: WO2012/026491

Non-patent Literature

Non-Patent Literature 1: Mummery, C., et al., Differentiation of human embryonic stem cells to cardiomyocytes: role of coculture with visceral endoderm-like cells. Circulation. 107(21), 2733-40 (2003).
Non-Patent Literature 2: Yang, L., et al., Human cardiovascular progenitor cells develop from a KDR+ embryonic-stem-cell-derived population. Nature. 453(7194), 524-8 (2008).
Non-Patent Literature 3: Leschik, J., et al., Cardiac commitment of primate embryonic stem cells. Nat Protoc. 3(9), 1381-7 (2008).
Non-Patent Literature 4: Paul, W B., et al., A Universal System for Highly Efficient Cardiac Differentiation of Human Induced Pluripotent Stem Cells That Eliminates Interline Variability. PLoSone. 6(4), e18293 (2011).
Non-Patent Literature 5: Wang, H., et al., Cardiac induction of embryonic stem cells by a small molecule inhibitor of Wnt/β-catenin signaling. ACS Chem Biol. 6(2), 192-7 (2011).
Non-Patent Literature 6: Iwamoto, R., et al., Heparin-binding EGF-like growth factor and ErbB signaling is essential for heart function. Proc Natl Acad Sci USA. 100(6), 3221-6 (2003).
Non-Patent Literature 7: Minami, I., et al., A Small Molecule that Promotes Cardiac Differentiation of Human Pluripotent Stem Cells under Defined, Cytokine- and Xeno-free Conditions. Cell Rep. 2012 Nov. 29; 2(5):1448-60. doi: 10.1016/j.celrep.2012.09.015. Epub 2012 Oct. 25.

SUMMARY OF INVENTION

An object of the present invention is to provide a composition and a method which allow cardiac differentiation of a pluripotent stem cell efficiently and at a low cost.

The present invention provides a composition for promoting cardiac differentiation of a pluripotent stem cell containing an EGFR inhibitor.

The present invention also provides a kit for promoting cardiac differentiation containing an EGFR inhibitor.

The present invention also provides a method for inducing cardiac differentiation of a pluripotent stem cell comprising culturing the pluripotent stem cell in a medium containing an EGFR inhibitor.

The present invention enables induction of cardiac differentiation of a pluripotent stem cell and preparation of a cardiomyocyte efficiently and at a low cost.

DESCRIPTION OF EMBODIMENTS

Figure 1:
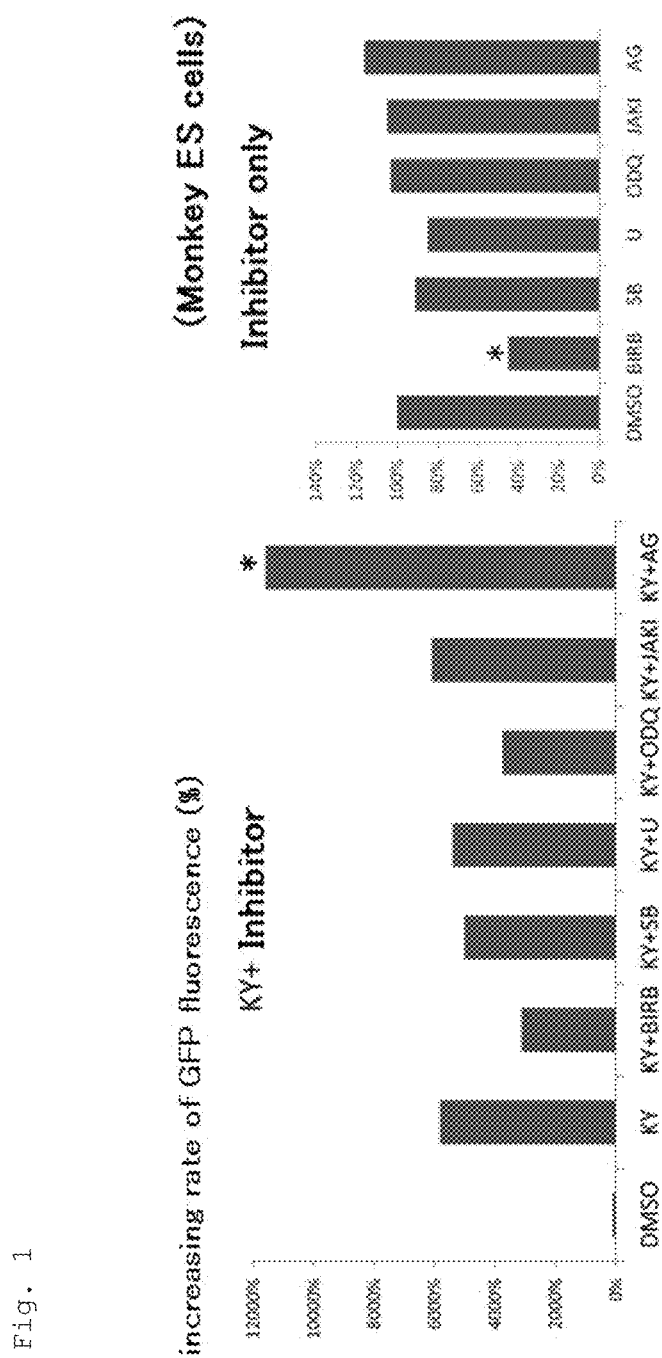
FIG. 1 shows the effects of various inhibitors to promote cardiac differentiation. KY: KYO2111, SB: SB203580, BIRB: BIRB796, U: U0126, JAKI: tyrphostin AG490, AG: AG1478.

The composition for promoting cardiac differentiation of a pluripotent stem cell of the present invention contains an epidermal growth factor (EGF) receptor (EGFR) inhibitor. "EGFR inhibitor" herein used refers to any substance that inhibits signaling from EGFR, including, but not limited to, low molecular weight compounds, nucleic acids, peptides, and antibodies. Examples of the EGFR inhibitor include AG1478, gefitinib, afatinib, ARRY334543, AST1306, AZD8931, BIBU1361, BIBX1382, BPDQ, BPIQ-I, BPIQ-II, canertinib, CL-387,785, CUDC101, dacomitinib, vandetanib, EGFR inhibitor III (N-(4-((3,4-dichloro-6-fluorophenyl)amino)-quinazoline-6-yl)-2-chloroacetamide, CAS 733009-42-2), EGFR/ErbB-2 inhibitor (4-(4-benzyloxyanilino)-6,7-dimethoxyquinazoline, CAS 179248-61-4), erlotinib, GW583340, GW2974, HDS029, lapatinib, WHI-P154, OSI-420, PD153035, PD168393, PD174265, pelitinib, Compound 56, XL657, PP3, AG-490, AGS55, tyrphostin B42, tyrphostin B44, AG556, AG494, AG825, RG-13022, DAPH, EGFR Inhibitor (cyclopropanecarboxylic acid (3-(6-(3-trifluoromethyl-phenylamino)-pyrimidin-4-ylamino)-phenyl)-amide, CAS 879127-07-8), erbstatin analog (methyl 2,5-dihydroxycinnamate, CAS 63177-57-1), JNJ28871063, tyrphostin 47, lavendustin A, lavendustin C, lavendustin C methylate, LFM-A12, TAK165, TAK285, tyrphostin 51, tyrphostin AG183, tyrphostin AG528, tyrphostin AG99, tyrphostin RG14620, WZ3146, WZ4002, WZ8040, butein, and tyrphostin AG112. In an embodiment, the EGFR inhibitor is an EGFR inhibitor having quinazoline structure, such as AG1478, gefitinib, afatinib, ARRY334543, AST1306, AZD8931, BIBU1361, BIBX1382, BPDQ, BPIQ-I, BPIQ-II, canertinib, CL-387,785, CUDC101, dacomitinib, vandetanib, EGFR inhibitor III (CAS 733009-42-2), EGFR/ErbB-2 inhibitor (CAS 179248-61-4), erlotinib, GW583340, GW2974, HDS029, lapatinib, WHI-P154, OSI-420, PD153035, PD168393, PD174265, pelitinib, Compound 56, or XL657, or PP3. EGFR inhibitors preferred for the present invention include AG1478, gefitinib, and PP3. EGFR inhibitors may be obtained, for example, from Santa Cruz Biotech.

The term "pluripotent stem cell" herein used refers to a cell having an ability to differentiate any type of cell constituting an adult body (pluripotency) and self-renewal capacity which is an ability to maintain the pluripotency during cell division. The "pluripotent stem cell" includes an embryonic stem cell (an ES cell), an embryonic germ cell (an EG cell), and an induced pluripotent stem cell (an iPS cells). The "pluripotent stem cell" may be a cell of any species with no limitation, and preferably a mammalian cell, and more preferably a rodent or primate cell. The present invention is particularly suitable for a monkey or human pluripotent stem cell.

An ES cell is a pluripotent stem cell derived from early embryo and may be established from inner cell mass of a blastocyst or post-implantation epiblast in early embryo. Examples of the ES cell include those described in the following references: human (Thomson J. A. et al., Science 282: 1145-1147 (1998), Biochem Biophys Res Commun. 345(3), 926-32 (2006); primates such as rhesus macaque and marmoset (Thomson J. A. et al., Proc. Natl. Acad. Sci. USA 92: 7844-7848 (1995); Thomson J. A. et al., Biol. Reprod. 55: 254-259 (1996)); rabbit (National Publication of International Patent Application No. 2000-508919); hamster (Doetshman T. et al., Dev. Biol. 127: 224-227 (1988)), hog (Evans M. J. et al., Theriogenology 33: 125128 (1990); Piedrahita J. A. et al., Theriogenology 34: 879-891 (1990); Notarianni E. et al., J. Reprod. Fert. 40: 51-56 (1990); Talbot N. C. et al., Cell. Dev. Biol. 29A: 546-554 (1993)), sheep (Notarianni E. et al., J. Reprod. Fert. Suppl. 43: 255-260 (1991)), cow (Evans M. J. et al., Theriogenology 33: 125-128 (1990); Saito S. et al., Roux. Arch. Dev. Biol. 201: 134-141 (1992)), and mink (Sukoyan M. A. et al., Mol. Reord. Dev. 33: 418-431 (1993)) (these references are herein incorporated by reference).

An EG cell is a pluripotent stem cell derived from a primordial germ cell, and examples include a human EG cell (Shamblott, et al., Proc. Natl. Acad. Sci USA 95: 13726-13731 (1998)) (the reference is herein incorporated by reference).

The term "iPS cell" herein used refers to a pluripotent stem cell induced from a cell other than a pluripotent stem cell such as a somatic cell and a tissue stem cell. Methods for preparing the iPS cell are described in the following references, for example: WO2007/069666, WO2009/006930, WO2009/006997, WO2009/007852, WO2008/118820, Cell Stem Cell 3(5): 568-574 (2008), Cell Stem Cell 4(5): 381-384 (2009), Nature 454: 646-650 (2008), Cell 136(3):411-419 (2009), Nature Biotechnology 26: 1269-1275 (2008), Cell Stem Cell 3: 475-479 (2008), Nature Cell Biology 11: 197-203 (2009), Cell 133(2): 250-264 (2008), Cell 131(5): 861-72 (2007), Science 318 (5858): 1917-20 (2007) (these references are herein incorporated by reference). However, a cell prepared by any method is included in the "iPS cell" of the present invention as long as it is a pluripotent stem cell which has been induced artificially.

The composition for promoting cardiac differentiation of the present invention may be used in combination with another agent that promotes cardiac differentiation such as a Wnt signaling inhibitor, a Wnt signaling activator, nitrovin or cytokines (combination of bFGF, BMP4, VEGF, DKK1 and Activin A). The term "agent that promotes cardiac differentiation" herein used refers to any substance which has an effect to promote cardiac differentiation. In a preferred embodiment, the composition for promoting cardiac differentiation of the present invention is used in combination with a Wnt signaling inhibitor and/or a Wnt signaling activator.

The "WNT signaling activator" as used herein refers to a substance which activates the WNT signaling pathway. Examples of the WNT signaling activator include a GSK3β inhibitor such as BIO or CHIR99021. In the present invention, two or more, for example 2, 3, or 4 WNT signaling activators may be used in combination.

The "WNT signaling inhibitor" as used herein refers to a substance which inhibits the WNT signaling pathway. Examples of the WNT signaling inhibitor include the compounds of formula (I) or salts thereof as described below, compounds such as IWP2, XAV939, and IWR1, and proteins such as IGFBP4 and Dkk1. Preferably, the WNT signaling inhibitor used in the invention is a compound, for example, a compound such as the compounds of formula (I) or salts thereof, IWP2, XAV939, and IWR1. In the present invention, two or more, for example 2, 3, or 4 WNT signaling inhibitors may be used in combination.

In an embodiment, the WNT signaling inhibitor is a compound represented by Formula (I):

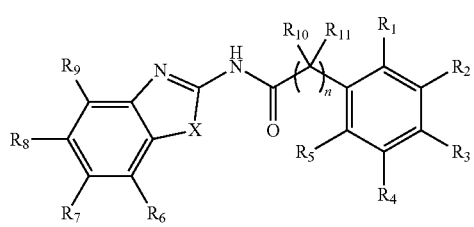

wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}$—$R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, or a salt thereof.

Examples of the linear or branched alkoxy group having 1 to 5 carbon atoms include a methoxy group, an ethoxy group, a propoxy group, an isopropoxy group, a butoxy group, an isobutoxy group, a sec-butoxy group, a tert-butoxy group and a pentyloxy group.

Examples of the linear or branched alkyl group having 1 to 5 carbon atoms include a methyl group, an ethyl group, a propyl group, an isopropyl group, a butyl group, an isobutyl group, a sec-butyl group, a tert-butyl group and a pentyl group.

Examples of the linear or branched acyl group having 1 to 5 carbon atoms include a formyl group, an acetyl group, a propionyl group, a butyryl group, an isobutyryl group, a valeryl group and an isovaleryl group.

Examples of the halogen atom include Cl, Br, I or F.

In a preferred embodiment, $R_1$ to $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—.

$R_2$ and $R_3$ are preferably a linear or a branched alkoxy group having 1 to 5 carbon atoms or join together to form —O—$CH_2$—O— or —O—$(CH_2)_2$—O—. More preferably, $R_2$ and $R_3$ are a methoxy group, an ethoxy group or a propoxy group. Further preferably, $R_2$ is a methoxy group and $R_3$ is a methoxy group, an ethoxy group or a propoxy group.

$R_1$, $R_4$ and $R_5$ are preferably a hydrogen atom.

In an embodiment, $R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—.

$R_6$ and $R_9$ are preferably each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, more preferably a hydrogen atom.

In a preferred embodiment, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted of substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—$CH_2$—O— or —O—$(CH_2)_2$—O—.

In an embodiment, $R_7$ is a hydrogen atom.

In an embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom, and examples of such A include a pyrrolidinyl, imidazolidinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl groups which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

$R_{10}$ and $R_{11}$ are preferably a hydrogen atom.

In a preferred embodiment, X is an oxygen atom; a sulfur atom; or a group —$NR_{15}$, wherein $R_{15}$ is a hydrogen atom, a linear or branched alkyl group having 1 to 5 carbon atoms, a linear or branched acyl group having 1 to 5 carbon atoms. X is preferably a sulfur atom.

In a preferred embodiment, n is an integer of 0 to 4. In a further preferred embodiment, n is an integer of 1 to 3, and more preferably n is 2 or 3.

Examples of the compound of Formula (I) or a salt thereof include the following compounds and salts thereof:

(1) the compounds represented by Formula (I):

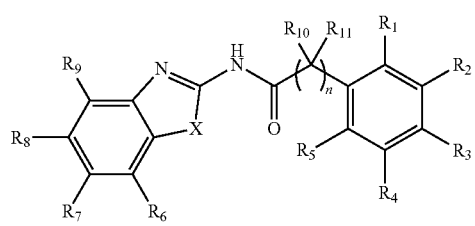

(I)

wherein
$R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, or salts thereof, (2) the compounds according to (1) above, wherein $R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, or salts thereof, (3) the compounds according to (2) above, wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—, and X is an oxygen atom; a sulfur atom; or a group —$NR_{15}$, wherein $R_{15}$ is a hydrogen atom, a linear or branched alkyl group having 1 to 5 carbon atoms, a linear or branched acyl group having 1 to 5 carbon atoms, or salts thereof, (4) the compounds according to (3) above, wherein $R_2$ and $R_3$ are a linear or a branched alkoxy group having 1 to 5 carbon atoms or join together to form —O—$CH_2$—O— or —O—$(CH_2)_2$—O—, $R_6$ and $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom, and

9

R$_7$ is a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom, R$_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, or R$_7$ and R$_8$ join together to form —O—CH$_2$—O— or —O—(CH$_2$)$_2$—O—,
or salts thereof, (5) the compounds according to (4) above,
wherein
R$_1$, R$_4$, R$_5$, R$_6$, R$_9$, R$_{10}$ and R$_{11}$ are a hydrogen atom,
R$_2$ and R$_3$ are a methoxy group, an ethoxy group or a propoxy group,
X is a sulfur atom, and
n is an integer of 0 to 4,
or salts thereof, (6) the compounds according to (5) above,
wherein
R$_7$ is a halogen atom, and
R$_8$ is a hydrogen atom,
or salts thereof, (7) the compounds according to (5) or (6) above,
wherein
R$_7$ is a methoxy group, and
R$_8$ is a methoxy group, an ethoxy group or a propoxy group,
or salts thereof, (8) the compounds according to any one of (5) to (7) above,
wherein
n is an integer of 1 to 3,
or salts thereof, (9) the compounds according to (1) above,
wherein
R$_1$, R$_4$, R$_5$, R$_6$, R$_8$, and R$_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom;
R$_2$ and R$_3$ are a linear or a branched alkoxy group having 1 to 5 carbon atoms or join together to form —O—CH$_2$—O— or —O—(CH$_2$)$_2$—O—;
R$_7$ is a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; and
X is an oxygen atom; a sulfur atom; or a group —NR$_{15}$, wherein R$_{15}$ is a hydrogen atom, a linear or branched alkyl group having 1 to 5 carbon atoms, or a linear or branched acyl group having 1 to 5 carbon atoms,
or salts thereof,

(10) the compounds according to (11) above,
wherein
R$_1$, R$_4$, R$_5$, R$_6$, R$_8$, and R$_9$ are a hydrogen atom;
R$_2$ and R$_3$ are a methoxy group, an ethoxy group or a propoxy group;

10

R$_{10}$ and R$_{11}$ are an hydrogen atom;
X is a sulfur atom;
A is a piperidinyl group, a piperazinyl group or a morpholinyl group which is unsubstituted or substituted with a linear or branched alkyl group having 1 to 5 carbon atoms; and
n is an integer of 0 to 4,
or salts thereof.

In an embodiment, the compound of Formula (I) or a salt thereof is a compound selected from the following compounds or a salt thereof:

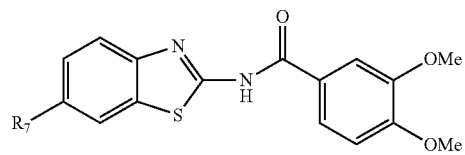

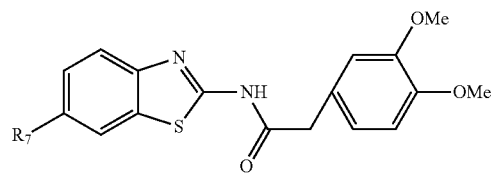

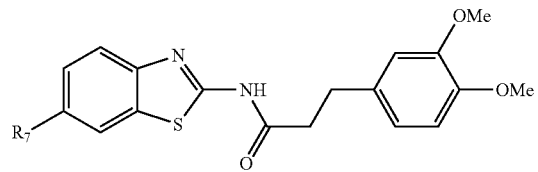

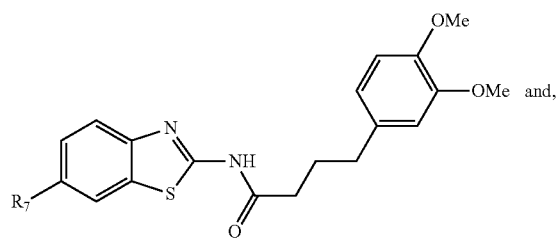 and,

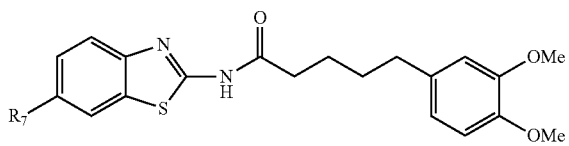

wherein R; is a halogen atom.

In a preferred embodiment, the WNT signaling inhibitor is a compound selected from the following group:

KY02111
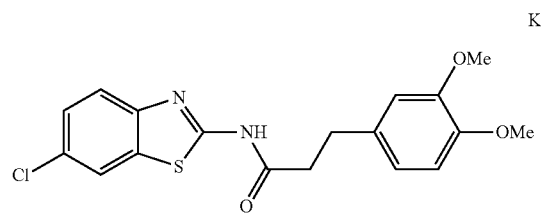
T61164
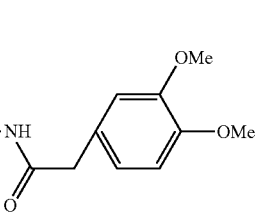
KY01045
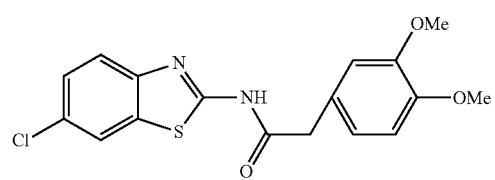
KY02109
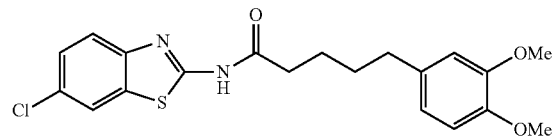
KY01043
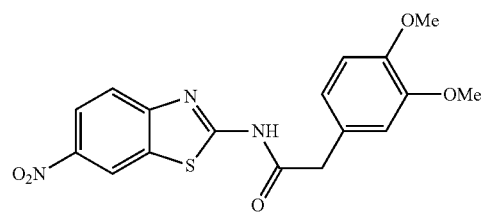
PB2852
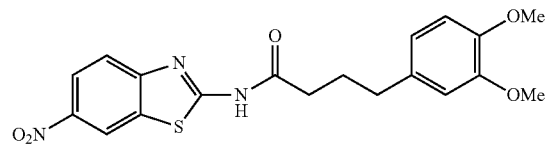
PB2572
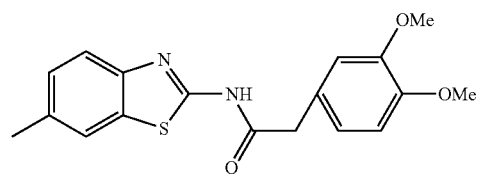
KY01041
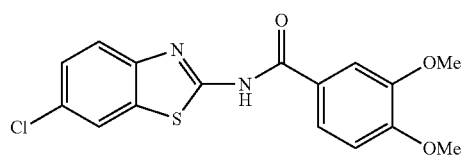
KY02114
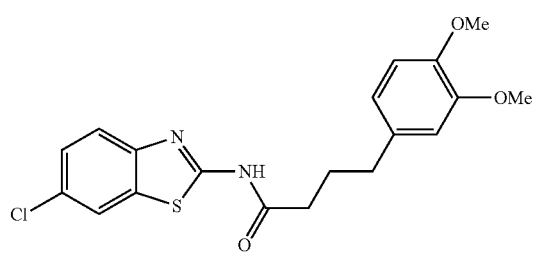
KY01040
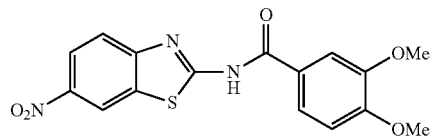
KY01042
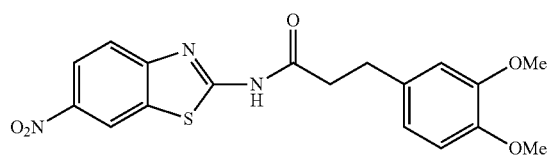
KY01046
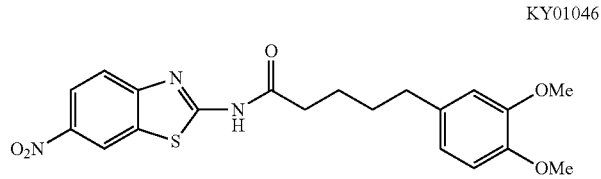
N11474
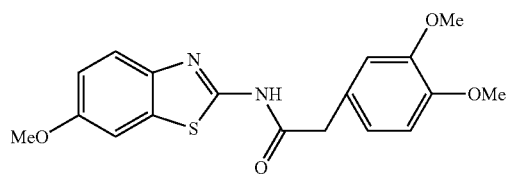
PB2570
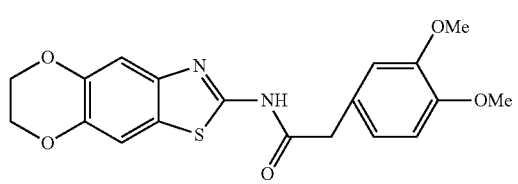

KY02104
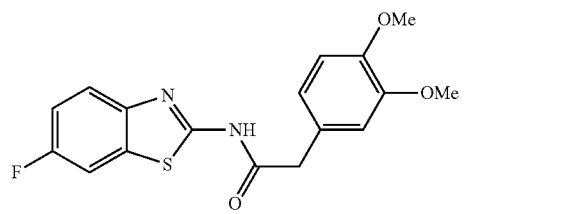
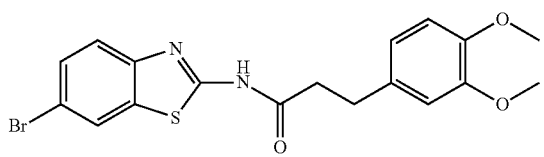
SO087
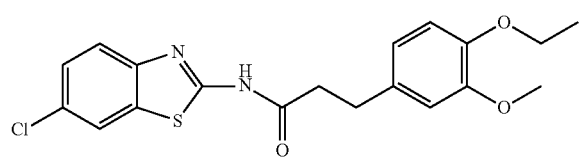
SO102
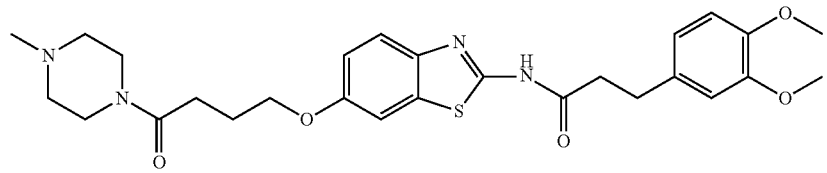
SO096
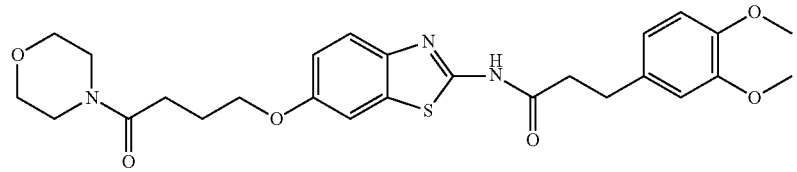
SO094
SO3031
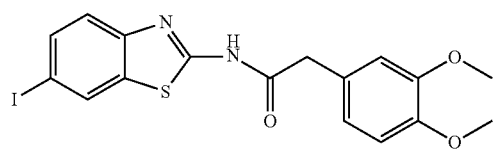
(KY01-I)
SO2031
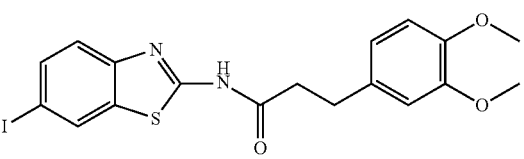
(KY02-I)
SO3042
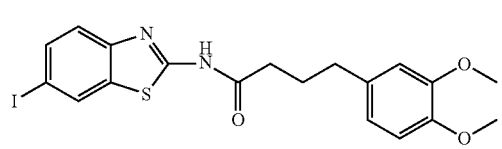
(KY03-I)
SO2077
or a salt thereof.
In a particularly preferred embodiment, the WNT signaling inhibitor is a compound selected from the following group:
-continued
KY01041
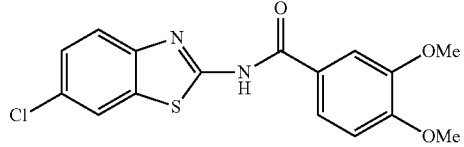
KY02111
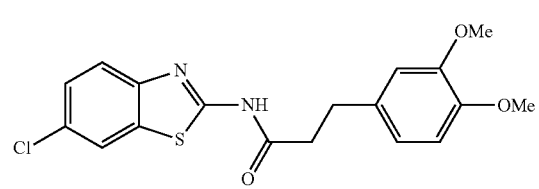
T61164
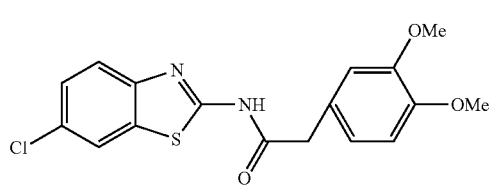

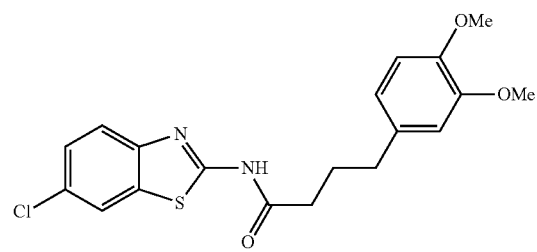
KY02114

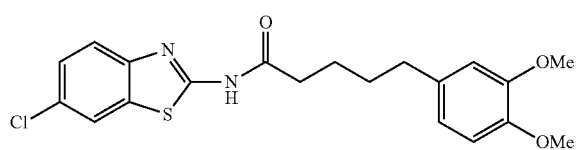
KY01045

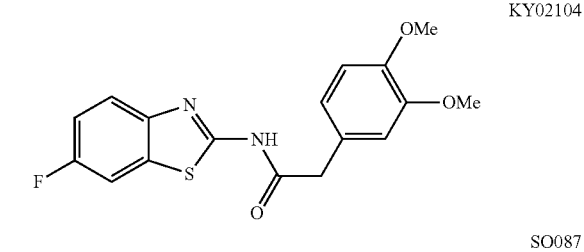
KY02104

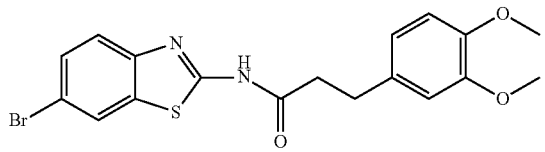
SO087

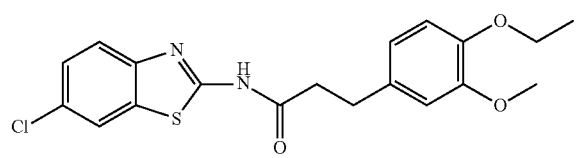
SO102

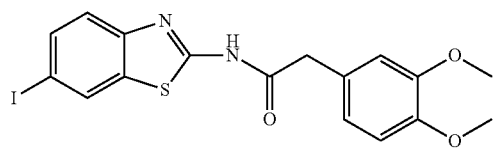
SO3031

(KY01-I)

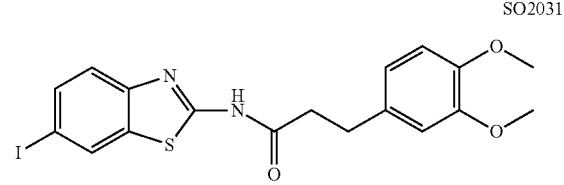
SO2031

(KY02-I)

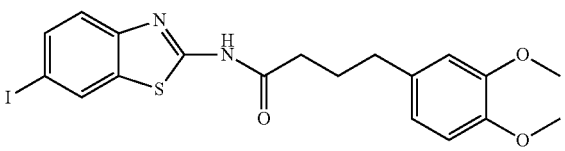
SO3042

(KY03-I)

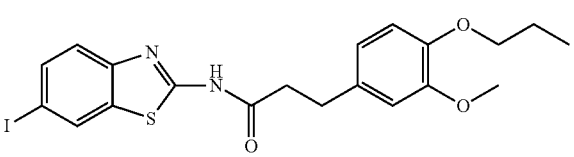
SO2077 or a salt thereof.

The compounds of Formula (I) can be synthesized by the known method (J. Med. Chem., 1965, 8 (5), pp 734-735) (incorporated herein by references) or in accordance with the methods described in WO2012/026491.

These compounds are described in, for example, J. Med. Chem., 1965, 8 (5), pp 734-735 (incorporated herein by references) (N11474, T61164). Also, they are available, for example, from UkrOrgSynthesis Ltd. (PB2852, PB2572, and PB2570) and ENAMINE (T61164).

The composition for promoting cardiac differentiation of a pluripotent stem cell provided by the present invention may be used in accordance with the method for inducing cardiac differentiation of a pluripotent stem cell provided by the present invention described below.

The kit for promoting cardiac differentiation of a pluripotent stem cell provided by the present invention comprises an EGFR inhibitor. The kit may further comprise an agent that promotes cardiac differentiation such as a Wnt signaling inhibitor or a Wnt signaling activator.

The method for inducing cardiac differentiation of a pluripotent stem cell provided by the present invention comprises culturing a pluripotent stem cell in a medium containing an EGFR inhibitor. The method is carried out in vitro. The medium used in the method of the present invention may be any conventional medium used for cardiac differentiation (i.e., "cardiac differentiation medium") of pluripotent stem cells and the medium is not limited to those having specific composition. Examples of the medium include IMDM-based cardiac differentiation medium (for example, the medium used in the examples), DMEM-based cardiac differentiation medium (for example, 200 ml of DMEM/F12 medium (Sigma), 50 ml of bovine fetal serum (GIBCO), 2.5 ml of MEM non-essential amino acid solution (Sigma), 2.5 ml of penicillin-streptomycin (GIBCO), 2.5 ml of 200 mM L-glutamine, and 2-mercaptoethanol), and Stem-Pro-34SFM (GIBCO)+BMP4 (10 ng/ml).

In an embodiment, the present invention provides a method for inducing cardiac differentiation of a pluripotent stem cell wherein a medium which does not contain serum (i.e., a serum-free medium) is used. When a serum-free medium is used, the medium preferably contains albumin. Examples of albumin include bovine serum albumin and human serum albumin. The serum-free medium containing albumin allows induction of cardiac differentiation of a pluripotent stem cell in the absence of proteins other than albumin, such as serum, cytokines, and feeder cells, and components derived from species of organism different from the pluripotent stem cell used in the method (i.e., xenogeneic components).

In the method of the invention, any conventional culture method suitable for cardiac differentiation of a pluripotent stem cell may be used. Examples of the culture method include adhesion culture, floating culture, and suspension culture. In an embodiment, the method of the invention does not use feeder cells such as END2 cells.

In the method of the invention, the period from the start of culture in a cardiac differentiation medium (i.e., culture for cardiac differentiation) to the start of culture in a medium containing an EGFR inhibitor, and the period of the culture in a medium containing an EGFR inhibitor may be appropriately determined. Preferably, when a monkey or human ES or iPS cell is used, the culture in a medium containing an EGFR inhibitor may be conducted for two days or more in the period from Day 2, Day 3, or Day 4 to Day 14 of the culture for cardiac differentiation (specifically, for 2, 3, 4, 5, 6, 1, 8, 9, 10, 11, or 12 days), preferably for 3 to 10 days, more preferably for 4 to 10 days, even more preferably for 4 to 8 days. For example, the culture in a medium containing an EGFR inhibitor is preferably conducted for 4 to 8 days in the period from Day 2, Day 3, or Day 4 to Day 10 of the culture for cardiac differentiation, for example Day 2 to Day 10 (for 8 days), Day 2 to Day 9 (for 7 days), Day 2 to Day 8 (for 6 days), Day 3 to Day 10 (for 7 days), Day 3 to Day 9 (for 6 days), Day 3 to Day 8 (for 5 days), Day 4 to Day 10 (for 6 days), Day 4 to Day 9 (for 5 days) or Day 4 to Day 8 (for 4 days) of the culture for cardiac differentiation.

The method of the invention may further comprise culturing a pluripotent stem cell in a medium containing a Wnt signaling activator and/or culturing a pluripotent stem cell in a medium containing a Wnt signaling inhibitor.

In an embodiment, the method of the invention comprises the step of culturing a pluripotent stem cell in a medium containing an EGFR inhibitor and a Wnt signaling inhibitor. The method may comprise the step of culturing a pluripotent stem cell in a medium containing an EGFR inhibitor or a Wnt signaling inhibitor in addition to the step of culturing the cell in the medium containing both of an EGFR inhibitor and a Wnt signaling inhibitor. For example, after the cell is cultured in a medium containing an EGFR inhibitor but not containing a Wnt signaling inhibitor, or in a medium containing a Wnt signaling inhibitor but not containing an EGFR inhibitor for one or two days, the medium may be replaced with a medium containing both of an EGFR inhibitor and an Wnt signaling inhibitor and the culture may be continued in the latter medium. Alternatively, throughout the whole period of the culture, the cell may be cultured in the medium containing both of an EGFR inhibitor and a Wnt signaling inhibitor. Also, after the cell is cultured in the medium containing both of an EGFR inhibitor and a Wnt signaling inhibitor, the cell may be cultured in the medium containing an EGFR inhibitor or a Wnt signaling inhibitor.

In an embodiment, the method of the invention comprises the steps of:
(1) culturing a pluripotent stem cell in a medium containing a Wnt signaling activator, and;
(2) culturing the cell in a medium containing an EGFR inhibitor after the step (1).

In the method, the period from the start of the culture for cardiac differentiation to the start of the step (1), the period from the end of the step (1) to the start of the step (2), and the periods of the steps (1) and (2) may be appropriately determined. The step (2) may start just after the end of the step (1), or after a certain period from the end of the step (1).

The Wnt signaling activator may be added at the early phase of cardiac differentiation of a pluripotent stem cell. The early phase of cardiac differentiation of a pluripotent stem cell means a stage at which differentiation of a pluripotent stem cell into mesoderm is induced and the expression of a mesoderm marker gene is increased. The differentiation into mesoderm may be determined by examining the expression of a mesoderm marker. Examples of the mesoderm marker includes T, MIXL1, and NODAL.

For example, when a monkey or human ES or iPS cell is used, the step (1) may be conducted at Day 0 to Day 2 or Day 0 to Day 3 of culture for cardiac differentiation, in other words, for 2 or 3 days from the start of culture for cardiac differentiation, and the step (2) may be conducted, for two days or more in the period from Day 2, Day 3, or Day 4 to Day 14 of the culture for cardiac differentiation (specifically, for 2, 3, 4, 5, 6, 7, 8, 9, 10, 11, or 12 days), preferably for 3 to 10 days, more preferably for 4 to 10 days, even more preferably for 4 to 8 days. Preferably, the step (2) is conducted for 4 to 8 days in the period from Day 2, Day 3, or Day 4 to Day 10 of the culture for cardiac differentiation, for example Day 2 to Day 10 (for 8 days), Day 2 to Day 9 (for 7 days), Day 2 to Day 8 (for 6 days), Day 3 to Day 10 (for 7 days), Day 3 to Day 9 (for 6 days), Day 3 to Day 8 (for 5 days), Day 4 to Day 10 (for 6 days) Day 4 to Day 9 (for 5 days) or Day 4 to Day 8 (for 4 days) of culture for cardiac differentiation.

In the method, preferably, the cell is cultured in a medium containing a Wnt signaling inhibitor in addition to an EGFR inhibitor in the whole or a part of the period of the step (2). The Wnt signaling inhibitor may be added at the middle phase of cardiac differentiation of a pluripotent stem cell. The middle phase of cardiac differentiation of a pluripotent stem cell means a stage at which differentiation of mesoderm into cardiomyocytes is induced. Differentiation into a cardiomyocyte may be detected from, for example, the number of beating cardiac colonies, expression of a cardiac marker, expression of an ion channel, or a response to an electrophysiological stimulus. Examples of the cardiac marker include α-MHC, β-MHC, cTnT, α-actinin, and NKX2.5. Examples of the ion channel include HCN4, Nav1.5, Cav1.2, Cav3.2 HERG1b and KCNQ1.

For example, after the cell is cultured in a medium containing an EGFR inhibitor but not containing a Wnt signaling inhibitor for one or two days, preferably for one day, the medium may be replaced with a medium containing an EGFR inhibitor and a Wnt signaling inhibitor and the culture is continued in the latter medium. Throughout the period of the step (2), the cell may be cultured in a medium containing both of an EGFR inhibitor and a Wnt signaling inhibitor. Alternatively, after the cell is cultured in a medium containing a Wnt signaling inhibitor but not containing an EGFR inhibitor for one or two days, the medium may be replaced with a medium containing an EGFR inhibitor and a Wnt signaling inhibitor and the culture may be continued in the latter medium. Further, after the cell is cultured in the medium containing both of an EGFR inhibitor and a Wnt signaling inhibitor, the cell may be cultured in the medium containing an EGFR inhibitor or a Wnt signaling inhibitor. The method enables efficient induction of cardiac differentiation of a pluripotent stem cell in floating culture.

Concentration of the EGFR inhibitor is not limited to specific concentrations in the present invention. When the EGFR inhibitor is gefitinib or AG1478, the EGFR inhibitor may be used at a final concentration of 100 nM to 100 µM, preferably 1 µM to 20 µM. When the EGFR inhibitor is PP3, the EGFR inhibitor may be used at a final concentration of 1 μM to 1 mM, preferably 10 μM to 100 μM.

Concentrations of the Wnt signaling activator and Wnt Wnt signaling inhibitor are not limited to specific concentrations in the present invention. When the Wnt signaling activator is BIO or CHIR99021, the Wnt signaling activator may be used at a final concentration of 100 nM to 100 μM, preferably 1 μM to 10 μM. When the Wnt signaling inhibitor is IWP2, XAV939, or IWR1, the Wnt signaling inhibitor may be used, for example, at a final concentration of 0.5 to 20 μM, preferably 1 to 10 μM. When the Wnt signaling inhibitor is a compound of Formula (I) or a salt thereof, the Wnt signaling inhibitor may be used, for example, at a final concentration of 0.1 to 20 μM, preferably 0.1 to 10 μM, more preferably 1 to 10 μM, depending on the compound or salt used.

The method of the invention may be used to prepare a cardiomyocyte. Production of a cardiomyocyte may be detected from, for example, the number of beating cardiac colonies, expression of a cardiac marker, expression of an ion channel, or a response to an electrophysiological stimulus. The cardiomyocyte prepared by the method of the invention may be used for evaluation of drug safety in vitro or as a cardiomyocyte for transplant to treat heart diseases.

In a further embodiment, the present invention provides a composition for promoting cardiac differentiation of a pluripotent stem cell comprising the compound of Formula (I) described above or a salt thereof which is used in combination with an EGFR inhibitor. The compound of Formula (I) or a salt thereof and the EGFR inhibitor in this embodiment are the same as those described for the composition for promoting cardiac differentiation of a pluripotent stem cell comprising an EGFR inhibitor.

In a further embodiment, the present invention provides use of an EGFR inhibitor for promoting cardiac differentiation of a pluripotent stem cell and use of an EGFR inhibitor for manufacturing a composition for promoting cardiac differentiation of a pluripotent stem cell. Such embodiment can be carried out according to the description provided for the composition for promoting cardiac differentiation and the method for inducing cardiac differentiation of the invention.

The present invention is described further in detail with reference to the following examples. The present invention is not limited by the examples in any sense.

EXAMPLES

1. Effect of EGFR Inhibitor to Promote Cardiac Differentiation of Monkey ES Cells in Adhesion Culture (1)

Monkey ES cells transfected with a GFP gene having a promoter of α-MHC, a cardiac differentiation marker, were plated on 6-well plates (ASAHI GLASS CO., LTD./5816-006: Ezview culture plate) at $2.0 \times 10^5$ cells/well and cultured in an IMDM-based cardiac differentiation medium containing 20% FBS (GIBCO 10099-141) (IMDM (Sigma) containing 20% FBS (Gibco), 1% MEM non-essential amino acid solution (Sigma), 1% penicillin-streptomycin (Gibco), 2 ml L-glutamine (Sigma), 0.001% 2-mercaptoethanol (Gibco), and 0.005N NaOH). During Days 4-8 of culture, KYO2111 (10 UM) was added together with AG1478, an EGFR inhibitor, or one of the following kinase inhibitors:
SB203580 (20 μM): p38MAPK inhibitor
BIRB796 (10 μM): p38MAPK inhibitor which has a stronger p38 inhibitory activity than SB
U0126 (10 μM): ERK/MAPKK (MEKK) inhibitor
ODQ (20 μM): NO-sensitive guanylyl cyclase inhibitor which inhibits cGMP production induced by NO
tyrphostin AG490 (5 μM): JAK2/3 inhibitor
AG1478 (20 μM): EGF receptor tyrosine kinase and Erb-B2 receptor inhibitor At Day 10 of culture, compounds that enhanced GFP fluorescence were identified by measuring GFP fluorescence with HCS (high contents screening) system (Olympus IX81 inverted microscope and Molecular device/MetaMorph imaging system).

Figure 2:
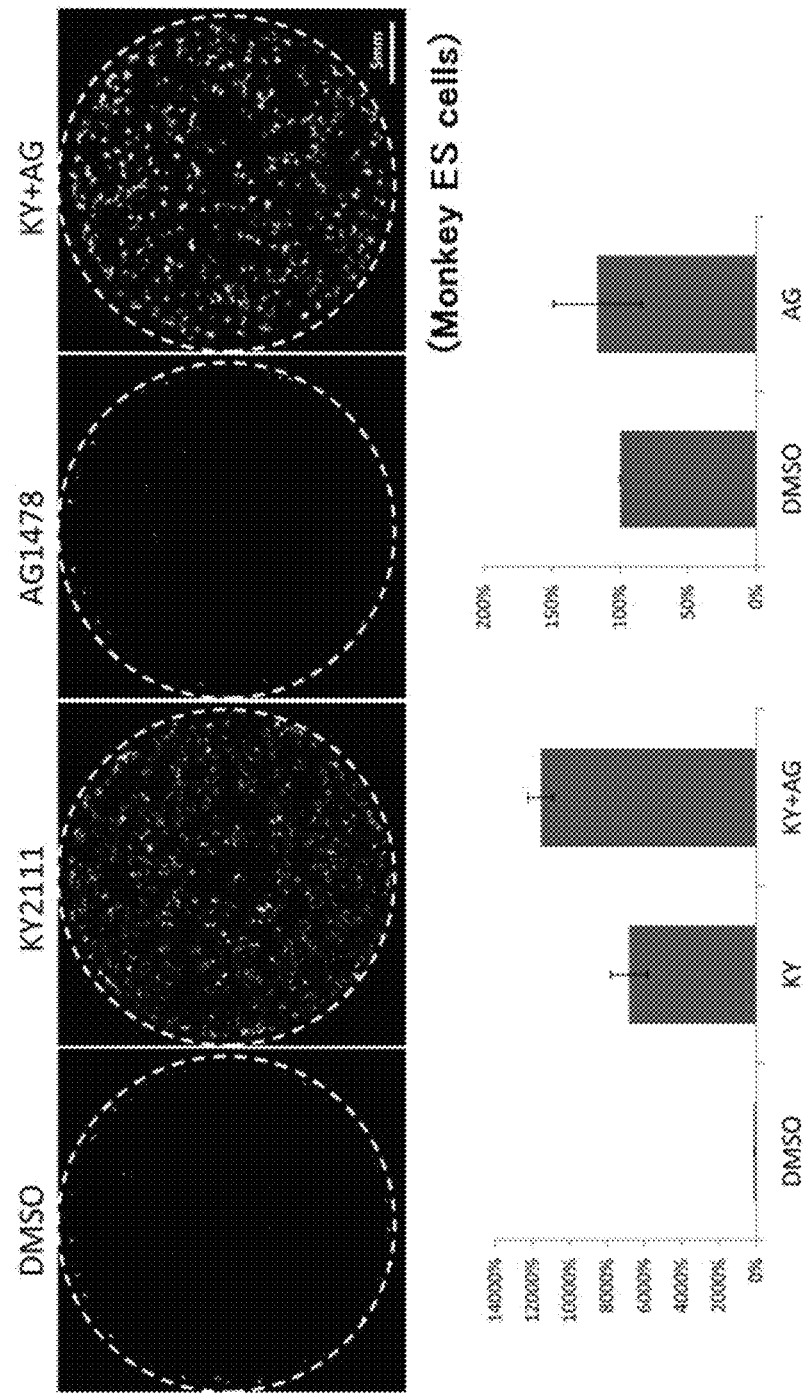
FIG. 2 shows the effect of an EGFR inhibitor (AG1478) to promote cardiac differentiation.
Figure 3:
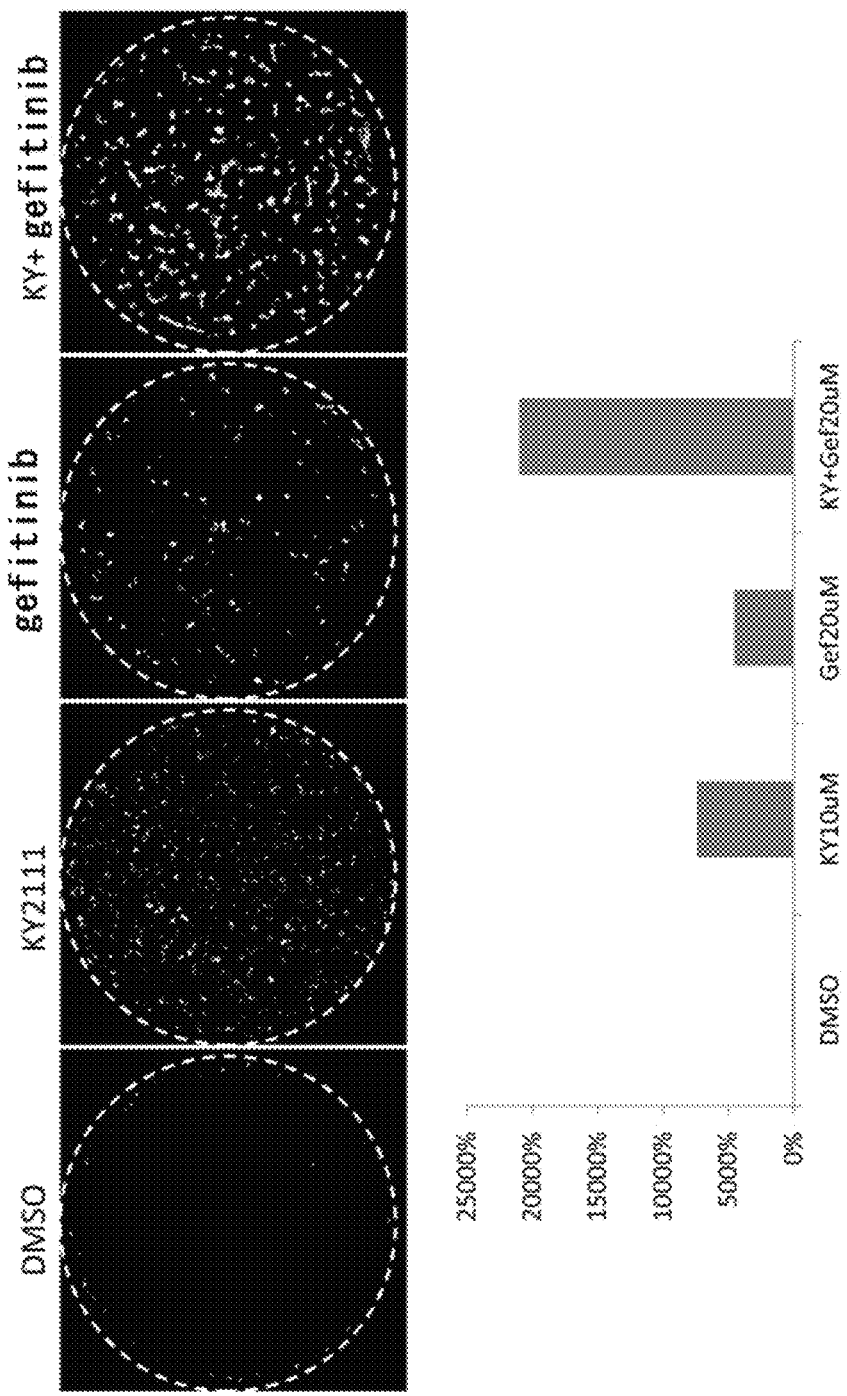
FIG. 3 shows the effect of an EGFR inhibitor (gefitinib) to promote cardiac differentiation.
Figure 4:
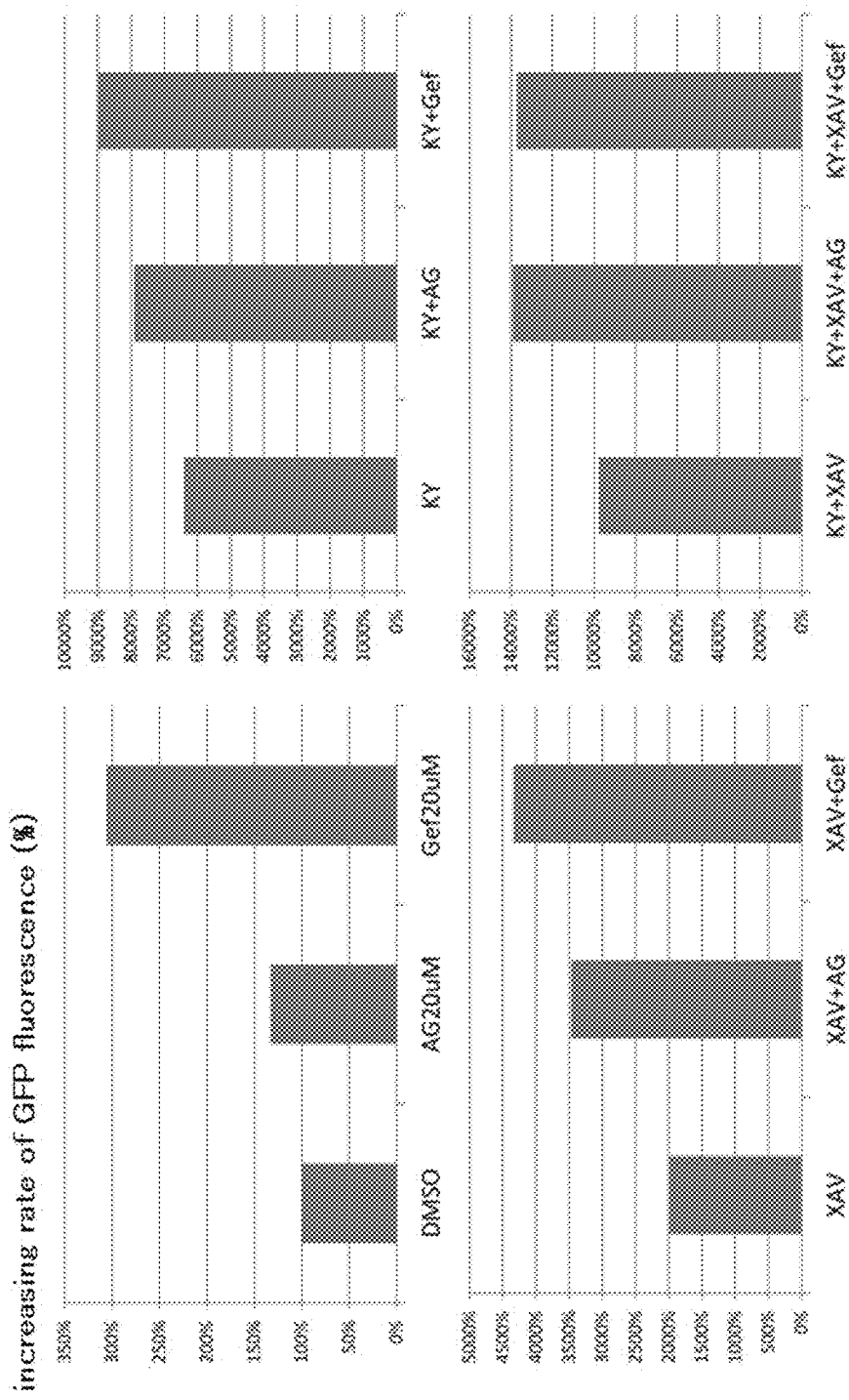
FIG. 4 shows the effects of EGFR inhibitors (AG1478 or gefitinib) to promote cardiac differentiation and synergistic effects of the EGFR inhibitors (AG1478 or gefitinib) and Wnt signaling inhibitors (KYO2111 and/or XAV939).

As a result, it was found that AG1478, an EGFR inhibitor, had the effect of promoting cardiac differentiation (FIGS. 1 and 2). Another EGFR inhibitor, gefitinib, was also found to have the effect of promoting cardiac differentiation (FIG. 3). In addition, it was revealed that AG1478 and gefitinib synergistically promoted cardiac differentiation when KYO2111 or XAV939 (WAKO), both of which are a Wnt signaling inhibitor, was added together (FIG. 4).

Figure 5:
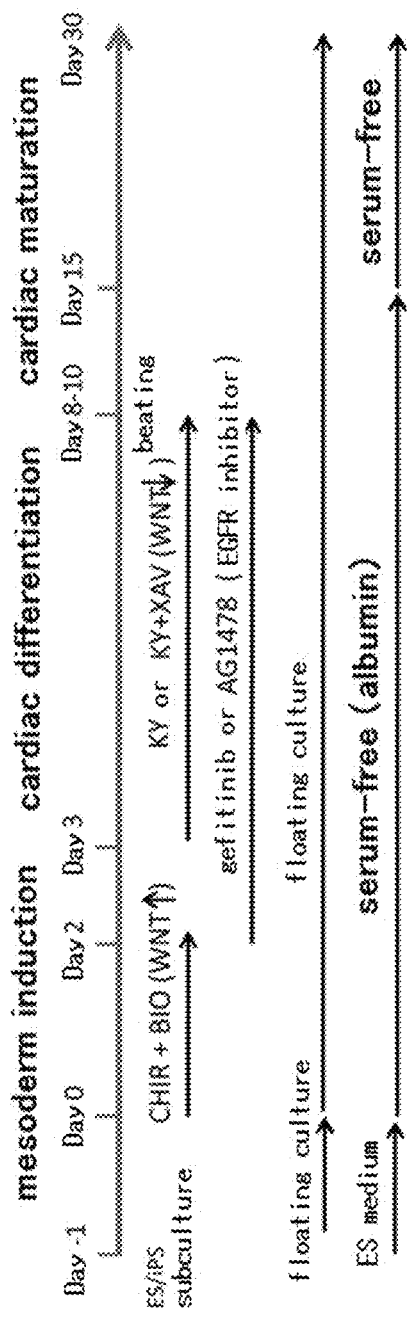
FIG. 5 shows the culture systems for inducing cardiac differentiation used in the examples.

2. Effect of EGFR Inhibitor to Promote Cardiac Differentiation of Human ES Cells and iPS Cells in Floating Culture Human ES cells or iPS cells subcultured with mouse feeder cells were collected. Colonies of the human ES cells or iPS cells ($3$-$10 \times 10^6$ cells/well) were plated on 6-well plates of Ultra-low culture dish (CORNING 3261), and cultured in an IMDM-based medium having a defined composition (IMDM (Sigma) containing 1% MEM non-essential amino acid solution (Sigma), 1% penicillin-streptomycin (Gibco), 2 mM L-glutamine (Sigma), 0.5 mM L-carnitine (Sigma), 0.001% 2-mercaptoethanol (Gibco), and 0.4% human serum albumin (Sigma)) in floating culture for 30 days (FIG. 5). During Days 0-2 of culture (for 2 days), CHIR99021 (Axon) (4 μM) and BIO (Calbiochem) (1 μM) were added, and during Days 3-9 of culture (for 6 days) KYO2111 (10 μM) and XAV939 (1 μM) were added. In addition to KYO2111 and XAV939, AG1478 or gefitinib, both of which are an EGFR inhibitor, was added at a concentration of 5-20 μM during Days 0-2 of culture (for 2 days), during Days 2-5 of culture (for 3 days), during Days 3-7 of culture (for 4 days) or during Days 2-9 of culture (for 7 days). The cardiac differentiation was evaluated by analyzing the percentage of cardiomyocytes with flow cytometry using an antibody against cardiac troponin T (cTnT), a specific marker of cardiac muscle at Day 30 of culture.

Figure 6:
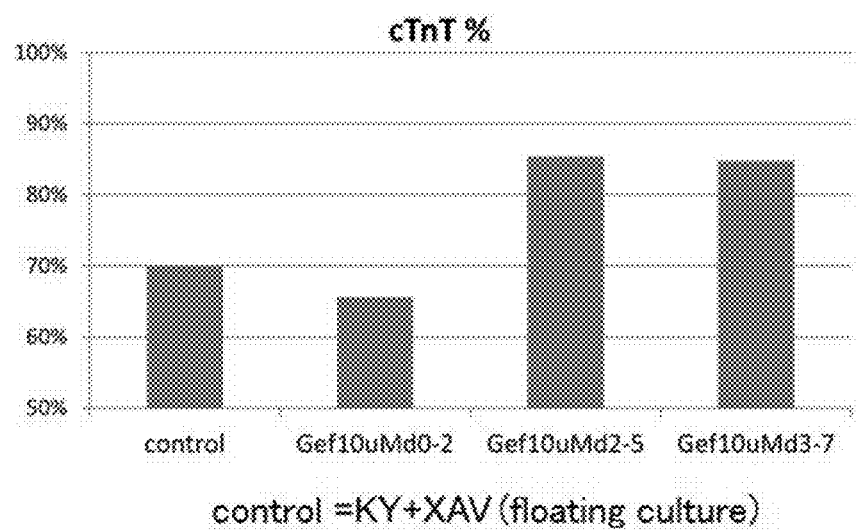
FIG. 6 shows the effect of an EGFR inhibitor (gefitinib) to promote cardiac differentiation of human ES cells (KhES-3) in cytokine- and Xeno-free conditions.
Figure 7:
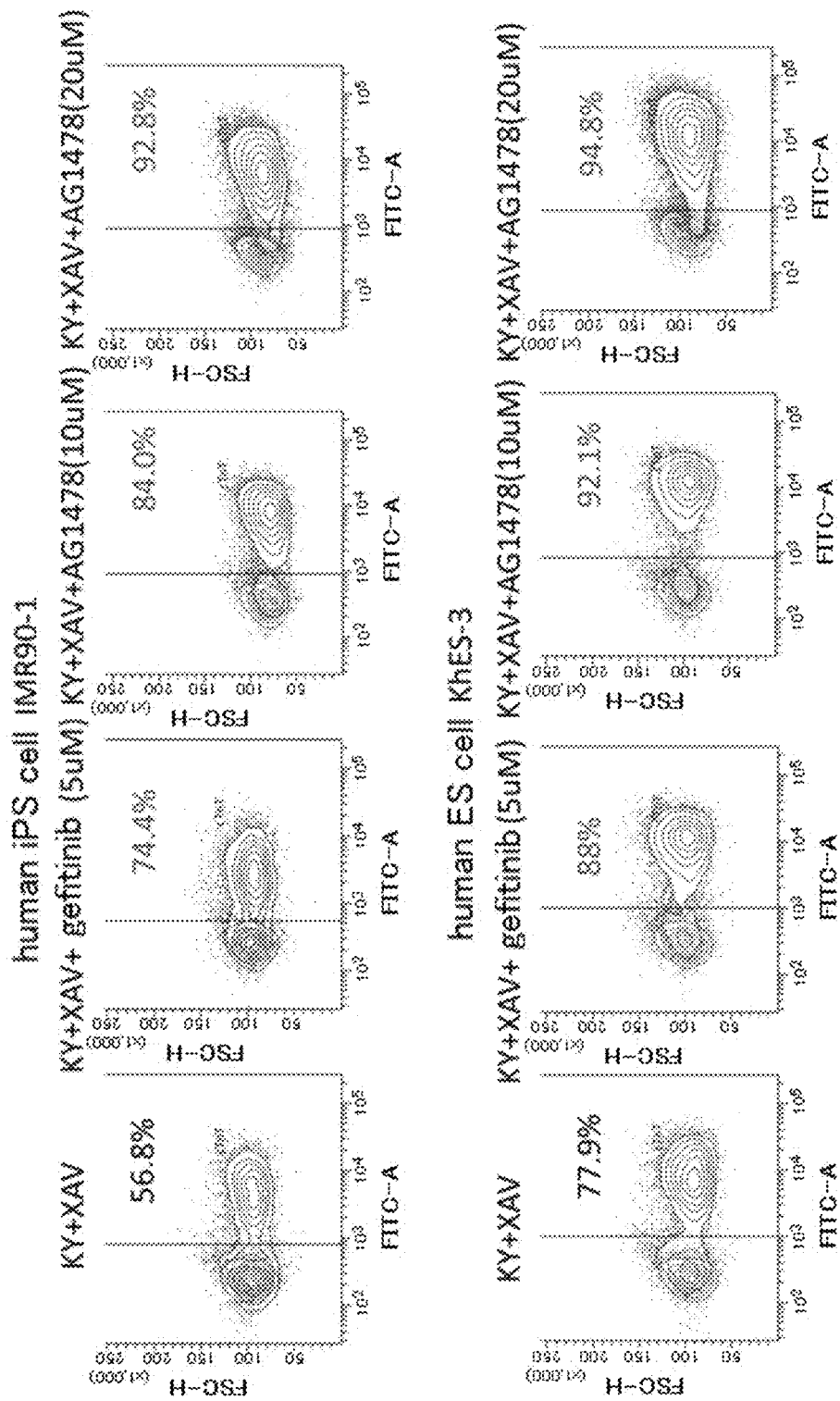
FIG. 7 shows the effects of EGFR inhibitors (AG1478 or gefitinib) to promote cardiac differentiation of human ES cells (KhES-3) and iPS cells (IMR90-1) in cytokine- and Xeno-free conditions.
Figure 8:
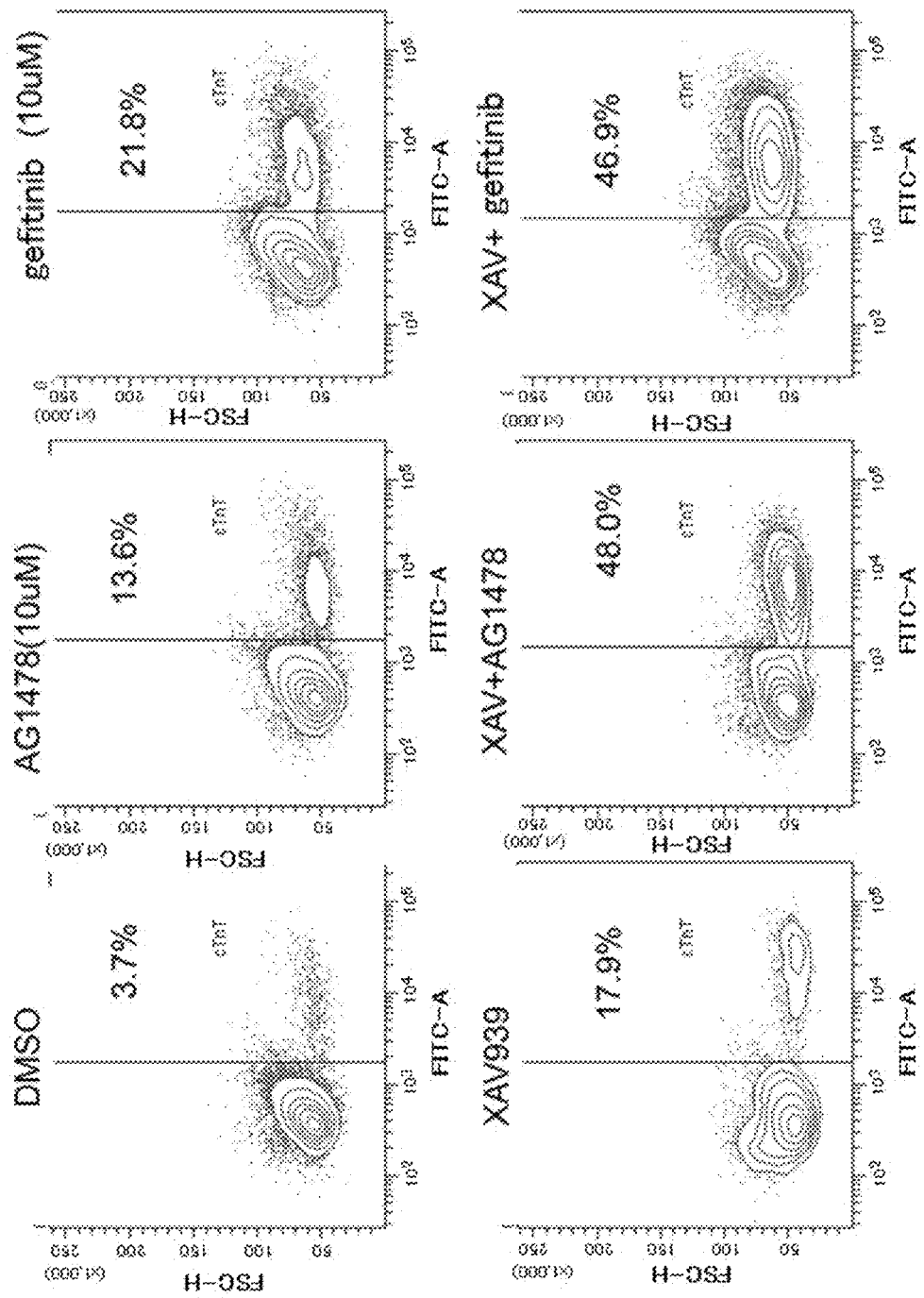
FIG. 8 shows the synergistic effects of EGFR inhibitors (AG1478 or gefitinib) and a Wnt signaling inhibitor (XAV939).

As a result, gefitinib (10 μM) did not promote cardiac differentiation of human ES cells (KhES-3) when added during Days 0-2 of culture, but remarkably increased the differentiation efficiency when added during Days 2-5 of culture or Days 3-7 of culture (FIG. 6). Furthermore, when AG1478 or gefitinib was added to human ES cells (KhES-3) and human iPS cells (IMR90-1) during Days 2-9 of culture at 5-20 μM, the cardiac differentiation efficiency was increased in both of human ES cells and iPS cells. In particular, AG1478 (20 μM) remarkably increased the percentage of cardiomyocytes up to 92-95% (FIG. 7). Either of AG1478 or gefitinib produced an effect to promote cardiac differentiation by itself (i.e. without addition of KYO2111 and XAV939) or in combination with XAV939 only (i.e. XAV+AG1478 or gefitinib) (FIG. 8). These results indicates that the combination of an EGFR inhibitor and a Wnt signaling activator and/or a Wnt signaling inhibitor provides a strong synergistic effect to promote cardiac differentiation.

3. Effect of EGFR Inhibitor to Promote Cardiac Differentiation of Human iPS Cells in Feeder-Free Sphere Culture System Human iPS cells (253G1) were cultured in sphere culture without feeder cells (feeder-free sphere culture). In detail, 253G1 cells subcultured with mouse feeder cells were collected, the cell cluster was passed through 50 μm mesh (CellTrics, PARTEC04004-2327) to give uniform cell clusters having the size of 80-120 μm, the cells were plated in 6-well plates of Ultra-low culture dish (CORNING 3261) and cultured in mTeSR1 medium (Stem Cell Technology 05850) containing 3% methylcellulose (R&D, HSC001) in floating culture until the size of the colonies of the iPS cells arrived at about 200-300 μm. The cells were subcultured more than 20 times by repeating the steps of this feeder-free sphere culture. The medium was replaced with an IMDM-based medium having a defined composition (IMDM (Sigma) containing 1% MEM non-essential amino acid solution (Sigma), 1% penicillin-streptomycin (Gibco), 2 mM L-glutamine (Sigma), 0.5 mM L-carnitine (Sigma), 0.001% 2-mercaptoethanol (Gibco), and 0.4% human serum albumin (Sigma)) and the cells were cultured in floating culture for 30 days (FIG. 5). During Days 0-2 of culture (for 2 days), CHIR99021 (4 μM) and BIO (1 μM) were added, and during Days 3-9 of culture (for 6 days) KYO2111 (10 μM) and XAV939 (1 μM) were added. In addition to KYO2111 and XAV939, AG1478 or gefitinib, both of which are an EGFR inhibitor, was added at a concentration of 10 μM during Days 3-9 of culture (for 6 days). The cardiac differentiation was evaluated by analyzing the percentage of cardiomyocytes with flow cytometry using an antibody against cardiac troponin T (cTnT), a specific marker of cardiac muscle at Day 30 of culture.

Figure 9:
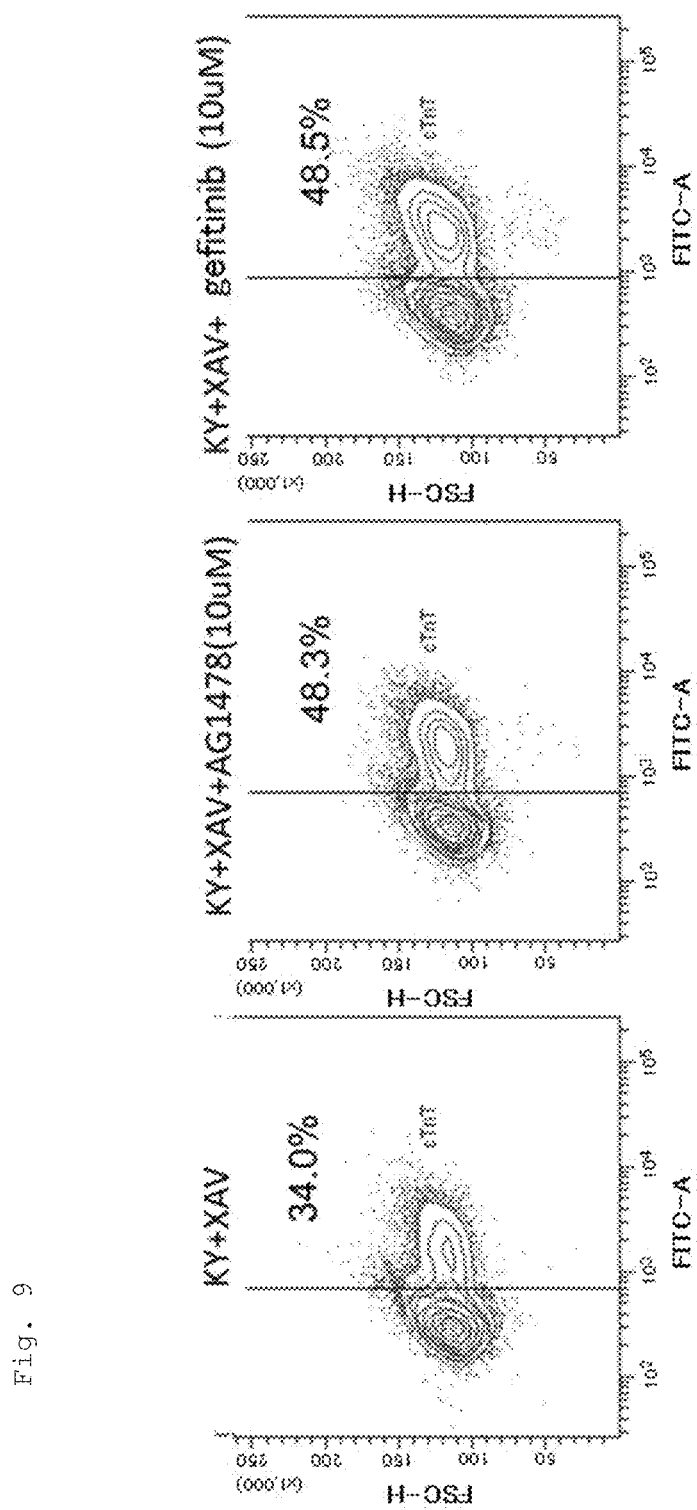
FIG. 9 shows direct cardiac differentiation of human iPS cells (253G1) from a sphere culture.

As a result, AG1478 and gefitinib increased the percentage of cardiomyocytes, which are the differentiated cells, from 34% to about 50% (FIG. 9). The result indicates that EGFR inhibitors increased the cardiac differentiation efficiency not only in human iPS cells cultured with mouse feeder cells but also in iPS cells in a feeder-free sphere culture system.

4. Effect of EGFR Inhibitor to Promote Cardiac Differentiation of Monkey ES Cells in Adhesion Culture (2)

Figure 10:
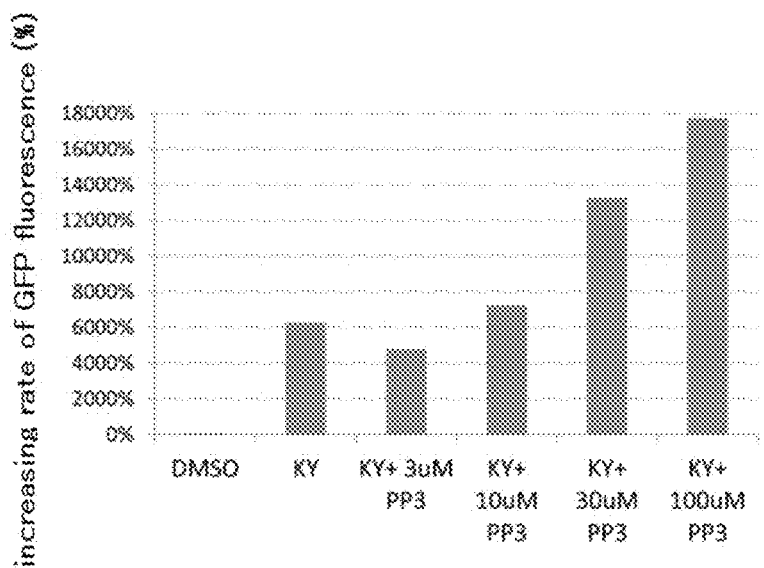
FIG. 10 shows a synergistic effect of an EGFR inhibitor (PP3) and a Wnt signaling inhibitor (KYO2111).

In the same manner as in Example 1 above, effect of PP3, an EGFR inhibitor, to promote cardiac differentiation was examined in monkey ES cells. During Days 4-8 of culture KYO2111 (10 μM) and PP3 (3 μM, 10 μM, 30 μM, or 100 μM) were added. As a result, PP3 was found to enhance the effect of KYO2111 to promote cardiac differentiation (FIG. 10). PP3 is an EGFR inhibitor that has the main structure different from that of AG1478 and gefitinib and has no inhibitory effect on Src kinase, which phosphorylates EGFR. The result indicates that agents that inhibit signaling from an EGF receptor have the effect of promoting cardiac differentiation.

Preparation Examples

SO03031 (KY01-I)

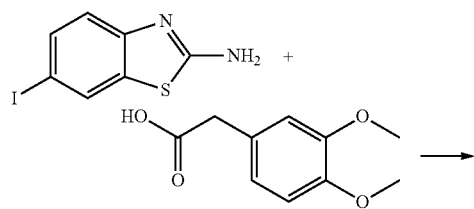

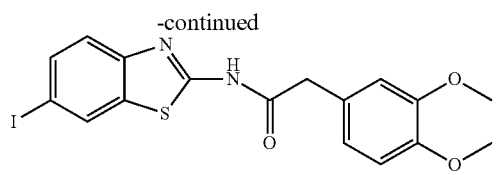

N,N-dimethylformamide solution (3 ml) containing 2-amino-6-iodobenzothiazole (200 mg, 0.723 mmol) and 3,4-dimethoxyphenylacetic acid (157 mg, 0.795 mmol) was added with N,N-diisopropylethylamine (139 μl, 0.803 mmol) and O-(6-chlorobenzotriazol-1-yl)-N,N,N',N'-tetramethyluronium hexafluorophosphate (360 mg, 0.870 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 167 mg of 2-(2-(3,4-dimethoxyphenyl)acetamide)-6-iodobenzothiazole was obtained in a yield of 50%.

$^1$H NMR (DMSO-$d_6$): δ 12.61 (s, 1H), 8.37 (s, 1H), 7.73-7.69 (m, 1H), 7.54 (d, J=8.0 Hz, 1H), 6.97-6.84 (m, 3H), 3.75-3.72 (m, 8H).

MS (ESI) Found; 455[M+H]$^+$

SO2031 (KY02-I)

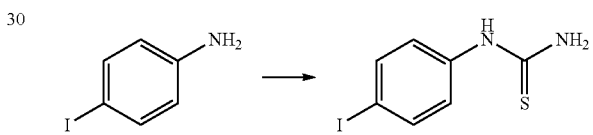

Dichloromethane solution (3 ml) of 4-iodoaniline (1.00 g, 4.57 mmol) was added with thiocarbonyldiimidazole (976 mg, 5.47 mmol) and stirred for 1.5 hours at room temperature. After addition of 25% ammonia solution (3 ml), the solution was stirred over night at room temperature. After completion of the reaction, the solvent was removed under reduced pressure, and the resulting deposits were filtered to obtain 889 mg of 1-(4-iodophenyl)thiourea at a yield of 59%.

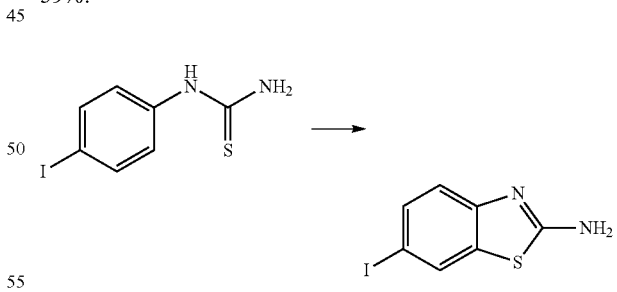

Chloroform suspension (7 ml) of 1-(4-iodophenyl)thiourea (889 mg, 3.19 mmol) was added with bromine (328 μl, 6.40 mmol), and heated to reflux and stirred for 6 hours. After the reaction was completed and the solvent was removed, the residue was added with dichloromethane and washed with saturated sodium bicarbonate solution and saturated sodium chloride solution. After the solution was dried over anhydrous sodium sulfate and the solvent was removed under reduced pressure, the resulting deposits were filtered to obtain 650 mg 2-amino-6-iodobenzothiazole in a yield of 73%.

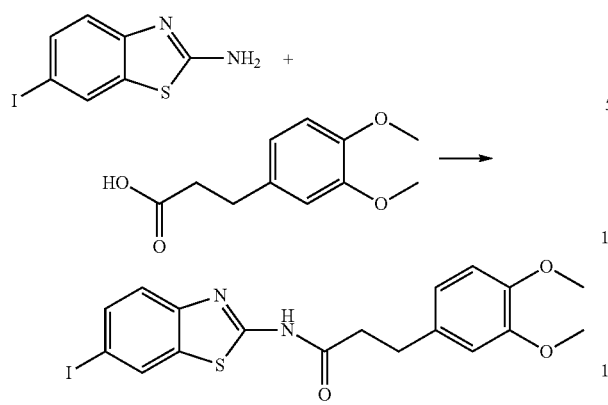

N,N-dimethylformamide solution (2 ml) containing 2-amino-6-iodobenzothiazole (100 mg, 0.362 mmol) and 3-(3,4-dimethoxyphenyl)propionic acid (91.4 mg, 0.435 mmol) was added with N,N-diisopropylethylamine (69.4 µl, 0.398 mmol) and O-(6-chlorobenzotriazol-1-yl)-N,N,N',N'-tetramethyluronium hexafluorophosphate (180 mg, 0.435 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 83 mg of 2-(3-(3,4-dimethoxyphenyl)propanamide)-6-iodobenzothiazole in a yield of 48%.

$^1$H NMR (DMSO-d$_6$): δ 12.42 (s, 1H), 8.37 (s, 1H), 7.72-7.69 (m, 1H), 7.52 (d, J=8.4 Hz, 1H), 6.85-6.83 (m, 2H), 6.75-6.72 (m, 1H), 3.71 (s, 3H), 3.69 (s, 3H), 2.90-2.76 (m, 4H).

MS (ESI) Found; 469[M+H]
SO3042 (KY03-I)

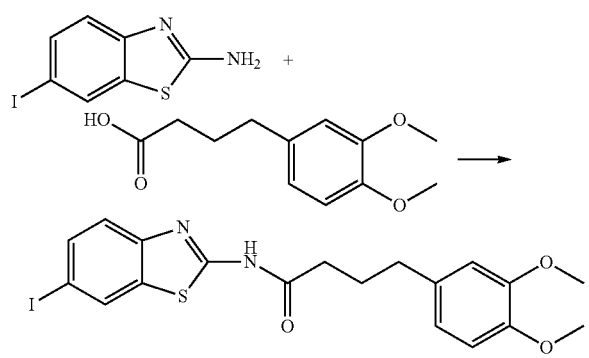

N,N-dimethylformamide solution (3 ml) containing 2-amino-6-iodobenzothiazole (250 mg, 0.905 mmol) and 4-(3,4-dimethoxyphenyl)butanoic acid (224 mg, 0.995 mmol) was added with N,N-diisopropylethylamine (174 µl, 0.995 mmol) and O-(6-chlorobenzotriazol-1-yl)-N,N,N',N'-tetramethyluronium hexafluorophosphate (450 mg, 1.09 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 131 mg of 2-(4-(3,4-dimethoxyphenyl)butanamide)-6-iodobenzothiazole was obtained in a yield of 30%.

$^1$H NMR (DMSO-d$_6$): δ 12.37 (s, 1H), 8.37 (s, 1H), 7.72-7.69 (m, 1H), 7.52 (d, J=8.4 Hz, 1H), 6.86-6.79 (m, 2H), 6.70 (d, J=8.0 Hz, 1H), 3.73 (s, 3H), 3.70 (s, 3H), 2.58-2.48 (m, 4H), 1.96-1.86 (m, 2H).

MS (ESI) Found; 483[M+H]$^+$
SO2077

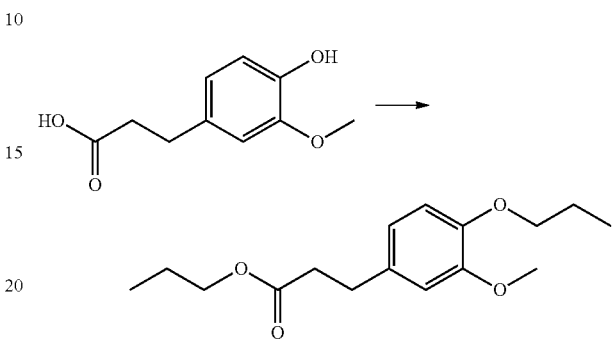

N,N-dimethylformamide solution (5 ml) containing 4-hydroxy-3-methoxypheny propionic acid (500 mg, 2.54 mmol) was added with potassium carbonate (881 mg, 6.37 mmol) and 1-bromopropane (692 µl, 7.65 mmol) and stirred over night at room temperature. After completion of the reaction, the solution was diluted with ethyl acetate and washed with water and saturated sodium chloride solution. The solution was dried over anhydrous sodium sulfate and the solvent was removed under reduced pressure. The residue was purified by silica gel column chromatography (n-hexane/ethyl acetate-4/1) and 590 mg of propyl 3-(3-methoxy-4-propoxyphenyl)propanoate was obtained in a yield of 82%.

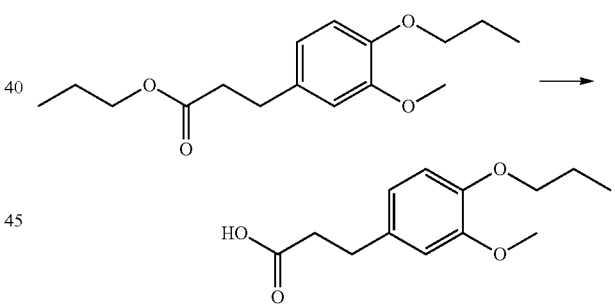

Propyl 3-(3-methoxy-4-propoxyphenyl)propanoate (590 mg, 2.10 mmol) was dissolved in 1,4-dioxane and added with 5 mol/l sodium hydroxide aqueous solution (1.68 ml) and the resulting solution was stirred over night at room temperature. After completion of the reaction, the solution was added with 6 mol/l hydrochloric acid and extracted with ethyl acetate. The organic layer was washed with saturated sodium chloride solution and dried over anhydrous sodium sulfate. The solvent was removed under reduced pressure and 438 mg of 3-(3-methoxy-4-propoxyphenyl)propionic acid was obtained in a yield of 87%.

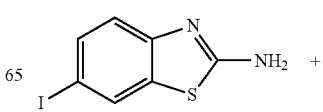

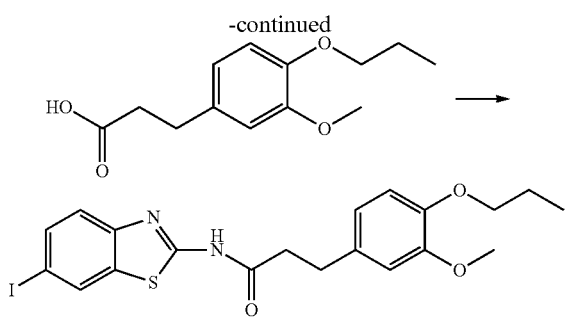

N,N-dimethylformamide solution (3 ml) containing 2-amino-6-iodobenzothiazole (200 mg, 0.723 mmol) and 3-(3-methoxy-4-propoxyphenyl)propionic acid (200 mg, 0.839 mmol) was added with N,N-diisopropylethylamine (140 μl, 0.803 mmol) and O-(6-chlorobenzotriazol-1-yl)-N,N,N',N'-tetramethyluronium hexafluorophosphate (360 mg, 0.870 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 217 mg of 2-(3-(3-methoxy-4-propoxyphenyl)propanamide)-6-iodobenzothiazole was obtained in a yield of 60%.

$^1$H NMR (DMSO-d$_6$): δ 12.42 (s, 1H), 8.38-8.37 (m, 1H), 7.72-7.69 (m, 1H), 7.54-7.51 (m, 1H), 6.85-6.82 (m, 2H), 6.72 (d, J=8.0 Hz, 1H), 3.86-3.82 (m, 2H), 3.72 (s, 3H), 2.87-2.78 (m, 4H), 1.72-1.65 (m, 2H), 094 (t, J=7.3 Hz, 3H).

MS (ESI) Found; 497[M+H]$^+$

The effect of SO3031 (KY01-I), SO2031 (KY02-I), SO3042 (KY03-I), and SO2077 to promote cardiac differentiation was confirmed by the methods described in the Examples of WO2012/026491.

The invention claimed is:

1. A method for inducing cardiac differentiation of a pluripotent stem cell in vitro, comprising the steps in a sequential order of:
   (1) first culturing the pluripotent stem cell in a medium containing a Wnt signaling activator, and then
   (2) culturing the cell in a medium containing an EGFR inhibitor after the step (1), wherein the cell is cultured in a medium containing an EGFR inhibitor and a Wnt signaling inhibitor, and optionally before or after, or both before and after the culture in the medium containing an EGFR inhibitor and a Wnt signaling inhibitor, the cell is cultured in a medium containing an EGFR inhibitor but not a Wnt signaling inhibitor and wherein the cell is cultured in floating culture,
   wherein the pluripotent stem cell is a monkey or human ES or iPS cell,
   the step (1) is conducted at Day 0 to Day 2 or Day 0 to Day 3 of culture for cardiac differentiation, and
   the step (2) is conducted for 3 to 10 days in the period from Day 2, Day 3, or Day 4 to Day 14 of the culture for cardiac differentiation when the step (1) is conducted at Day 0 to Day 2, or conducted for 3 to 10 days in the period from Day 3 or Day 4 to Day 14 of the culture for cardiac differentiation when the step (1) is conducted at Day 0 to Day 3.

2. The method according to claim 1, wherein the medium contains no protein other than albumin.

3. The method according to claim 1, which is a method for preparing a cardiomyocyte.

4. The method according to claim 1, wherein the EGFR inhibitor is selected from the group consisting of AG1478, gefitinib, afatinib, ARRY334543, AST1306, AZD8931, BIBU1361, BIBX1382, BPDQ, BPIQ-I, BPIQ-II, canertinib, CL-387,785, CUDC101, dacomitinib, vandetanib, EGFR Inhibitor III (CAS 733009-42-2), EGFR/ErbB-2 Inhibitor (CAS 179248-61-4), erlotinib, GW583340, GW2974, HDS029, lapatinib, WHI-P154, OSI-420, PD153035, PD168393, PD174265, pelitinib, Compound 56, XL657, PP3, AG-490, AG555, tyrphostin B42, tyrphostin B44, AG556, AG494, AG825, RG-13022, DAPH, EGFR Inhibitor (CAS 879127-07-8), erbstatin analog (CAS 3177-57-1), JNJ28871063, tyrphostin 47, lavendustin A, lavendustin C, lavendustin C methylate, LFM-A12, TAK165, TAK285, tyrphostin 51, tyrphostin AG183, tyrphostin AG528, tyrphostin AG99, tyrphostin RG14620, WZ3146, WZ4002, WZ8040, Butein, and tyrphostin AG112.

5. The method according to claim 1, wherein the EGFR inhibitor is selected from the group consisting of AG1478, gefitinib, and PP3.

6. The method according to claim 1, wherein the Wnt signaling inhibitor is a compound represented by Formula (I):

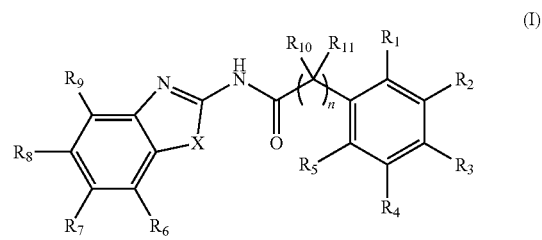

wherein
R$_1$ to R$_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —NR$_{13}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom; wherein two adjacent groups among R$_1$ to R$_5$ may join together to form —O—CH$_2$—O— or —O—(CH$_2$)$_2$—O—, R$_6$ to R$_9$ are each independently a hydrogen atom, a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—CH$_2$—O— or —O—(CH$_2$)$_2$—O—, $R_{10}$ to $R_{11}$ are each independently a hydrogen atom; or a linear or branched alkyl group having 1 to 5 carbon atoms, X is —CR$_{14}$, wherein R$_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —NR$_{15}$, wherein R$_{15}$ is a hydrogen atom, a linear or branched alkyl group having 1 to 5 carbon atoms, or a linear or branched acyl group having 1 to 5 carbon atoms, and n is an integer of 0 to 6, or a salt thereof.

7. The method according to claim 6, wherein in Formula (I)

$R_1$, $R_4$, $R_5$, $R_6$, $R_8$, $R_9$, $R_{10}$, and $R_{11}$ are a hydrogen atom, $R_2$ and $R_3$ is a methoxy group, an ethoxy group or a propoxy group, $R_7$ is a halogen atom, X is a sulfur atom, and n is an integer of 0 to 4.

8. The method according to claim 7, wherein in Formula (I)

$R_2$ is a methoxy group, and $R_3$ is a methoxy group, an ethoxy group or a propoxy group.

9. The method according to claim 1, wherein the Wnt signaling inhibitor is a compound selected from the group consisting of

KY02111

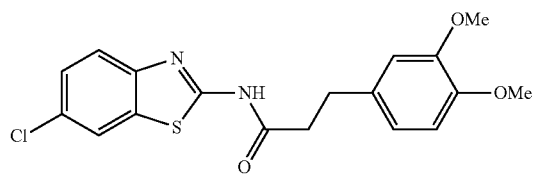

KY01041

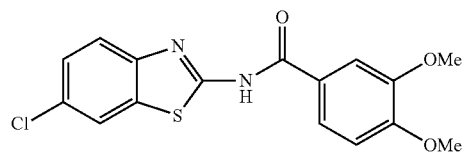

T61164

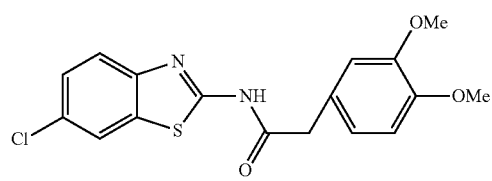

KY02114

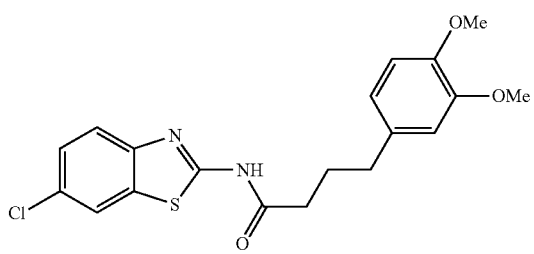

KY01045

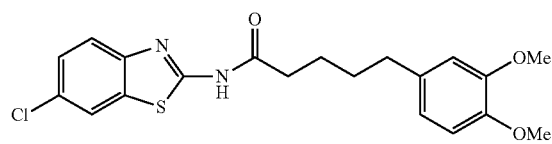

KY01040

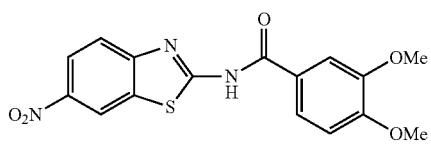

KY02109

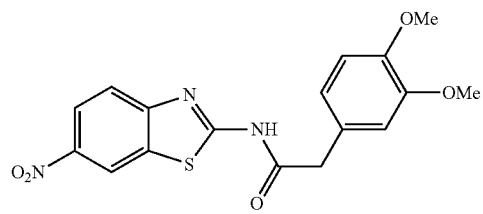

KY01042

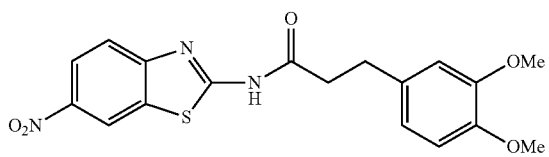

KY01043

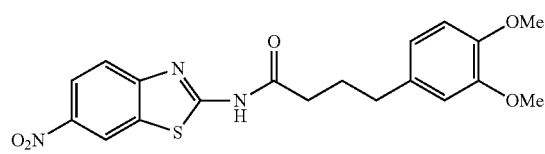

KY01046

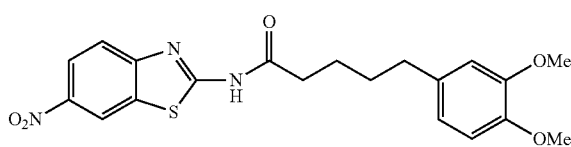

PB2852 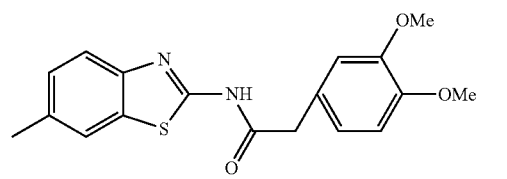
PB2572 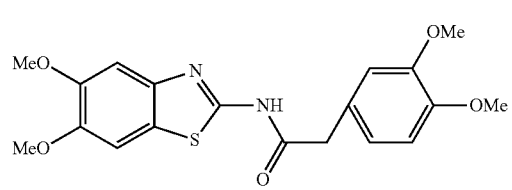
KY02104 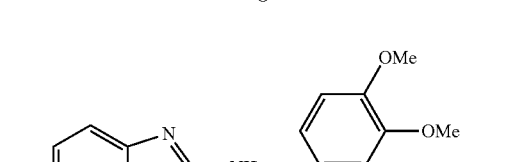
N11474 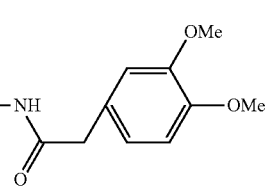
PB2570
SO087
SO102 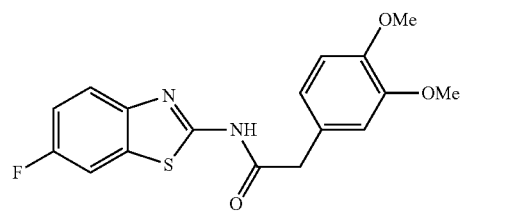
SO096 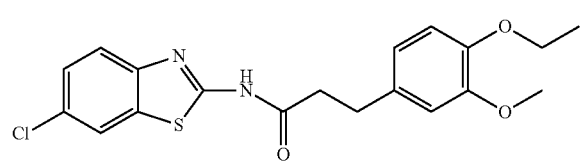
SO094 
SO3031 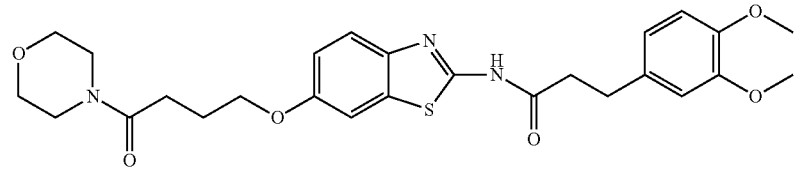
SO2031
(KY01-I) 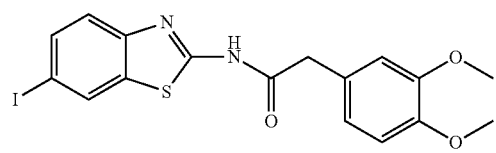
(KY02-I)
SO3042 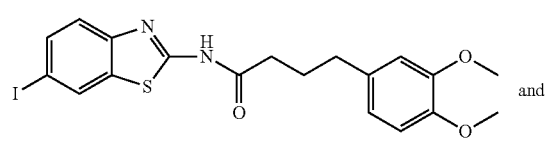
and
(KY03-I)
SO2077 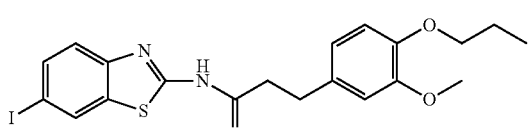
or a salt thereof.

10. The method according to claim 1, wherein the Wnt signaling inhibitor is selected from the group consisting of IWP2, XAV939, and IWR1.

11. The method according to claim 1, wherein the Wnt signaling activator is selected from the group consisting of BIO and CHIR99021.

12. The method according to claim 1, wherein two or more Wnt signaling inhibitors and two or more Wnt signaling activators are used in combination.

13. The method according to claim 12, wherein
the EGFR inhibitor is selected from the group consisting of AG1478, gefitinib, and PP3;
the Wnt signaling inhibitors are a compound represented by Formula (I):

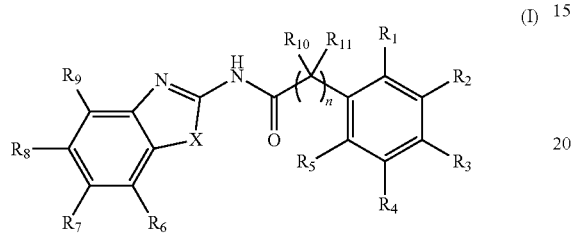

wherein $R_1$, $R_4$, $R_5$, $R_6$ $R_8$, $R_9$, $R_{10}$, and $R_{11}$ are a hydrogen atom, $R_2$ and $R_3$ is a methoxy group, an ethoxy group or a propoxy group, $R_7$ is a halogen atom, X is a sulfur atom, and n is an integer of 0 to 4, and a Wnt signaling inhibitor selected from the group consisting of IWP2, XAV939, and IWR1; and the Wnt signaling activators are BIO and CHIR99021.

14. The method according to claim 13, wherein the EGFR inhibitor is AG1478 or gefitinib; and the Wnt signaling inhibitors are the compound represented by Formula (I) and XAV939.

* * * * *